(12) United States Patent
Miao et al.

(10) Patent No.: US 12,428,476 B2
(45) Date of Patent: Sep. 30, 2025

(54) SYSTEM AND METHODS RELATING TO CHIMERIC AUTOANTIBODY RECEPTORS

(71) Applicant: Valkyr, Inc., Charlotte, NC (US)

(72) Inventors: Brenda Y. Miao, Fremont, CA (US); Jayanth Venkata Nagendra S Batchu, Charlotte, NC (US)

(73) Assignee: Valkyr, Inc., Charlotte, NC (US)

( * ) Notice: Subject to any disclaimer, the term of this patent is extended or adjusted under 35 U.S.C. 154(b) by 939 days.

(21) Appl. No.: 16/927,924

(22) Filed: Jul. 13, 2020

(65) Prior Publication Data

US 2021/0040199 A1   Feb. 11, 2021

Related U.S. Application Data

(60) Provisional application No. 62/873,176, filed on Jul. 11, 2019.

(51) Int. Cl.
| | |
|---|---|
| C07K 16/28 | (2006.01) |
| A61K 40/10 | (2025.01) |
| A61K 40/22 | (2025.01) |
| A61K 40/24 | (2025.01) |
| A61K 40/31 | (2025.01) |
| A61K 40/40 | (2025.01) |
| A61K 40/41 | (2025.01) |
| C07K 14/74 | (2006.01) |
| C07K 16/30 | (2006.01) |

(52) U.S. Cl.
CPC .............. *C07K 16/28* (2013.01); *A61K 40/10* (2025.01); *A61K 40/22* (2025.01); *A61K 40/24* (2025.01); *A61K 40/31* (2025.01); *A61K 40/40* (2025.01); *A61K 40/416* (2025.01); *C07K 14/70539* (2013.01); *C07K 16/30* (2013.01); *C07K 2319/02* (2013.01); *C07K 2319/03* (2013.01)

(58) Field of Classification Search
CPC .. C07K 16/28; C07K 14/70539; C07K 16/30; C07K 16/18
See application file for complete search history.

(56) References Cited

U.S. PATENT DOCUMENTS

| | | | |
|---|---|---|---|
| 10,301,370 B2 | 5/2019 | Payne | |
| 11,365,262 B2* | 6/2022 | Pulé | ...................... C12N 5/0636 |
| 2017/0051035 A1* | 2/2017 | Payne | .................. C07K 14/705 |

FOREIGN PATENT DOCUMENTS

| | | |
|---|---|---|
| CN | 108795876 | 11/2018 |
| WO | 2013044225 A1 | 3/2013 |
| WO | 2017091546 A1 | 6/2017 |
| WO | 2017222593 A1 | 12/2017 |
| WO | 2019094847 | 5/2019 |

OTHER PUBLICATIONS

Liu et al., "Engineering switchable and programmable universal CARs for CAR T therapy". J Hematol Oncol 12, 69 (2019). (Year: 2019).*
Yakimchuk et al., "Aptamers and Affimers". Mater Methods 2015; 5:1417. pp. 1-15 (Year: 2015).*
Liu, D. et al., "Engineering switchable and programmable universal CARs for CAR T therapy", Journal of Hematology & Oncology, Jul. 4, 2019, vol. 12, article No. 69, pp. 1-9.
Ellebrecht, C. T. et al., "Reengineering chimeric antigen receptor T cells for targeted therapy of autoimmune disease", Science, Jul. 8, 2016, vol. 353, No. 6295, pp. 179-184.
Zhang, A.-H. et al., "Targeting Antigen-Specific B Cells Using Antigen-Expressing Transduced Regulatory T Cells", The Journal of Immunology, 2018, vol. 201, pp. 1434-1441.

* cited by examiner

*Primary Examiner* — Allison M Fox
*Assistant Examiner* — Hanan Isam Abuzeineh
(74) *Attorney, Agent, or Firm* — Loginov & Associates, PLLC; William A. Loginov

(57) ABSTRACT

Chimeric autoantibody receptors (CAARs) can include separate signaling and recognition constructs that are able to bind ligands that target autoantigens made of conventional amino acids, non-conventional amino acids, carbohydrates, or nucleic acids. Additionally, the present disclosure describes cells modified to express such constructs and the use of such constructs and/or cells in the treatment of autoimmune disease.

20 Claims, 12 Drawing Sheets

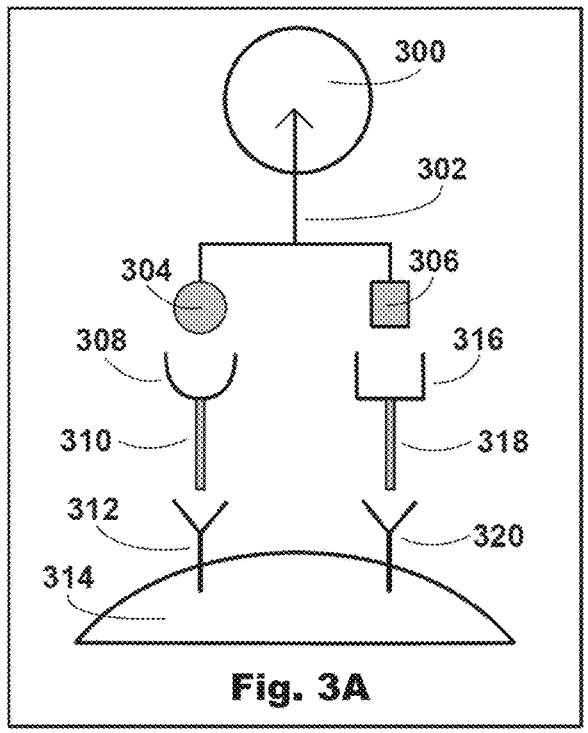
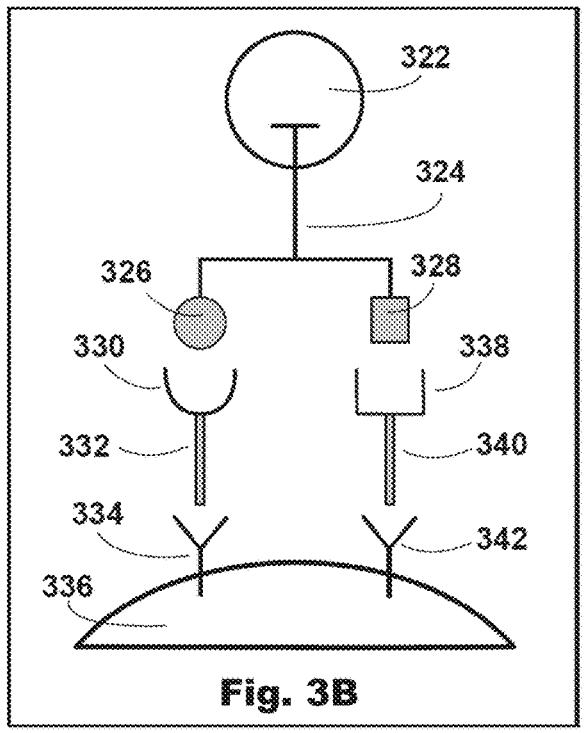
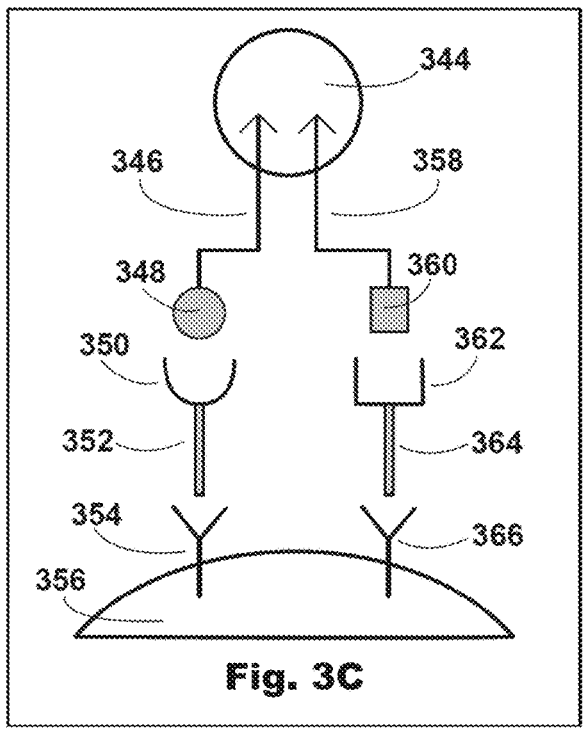
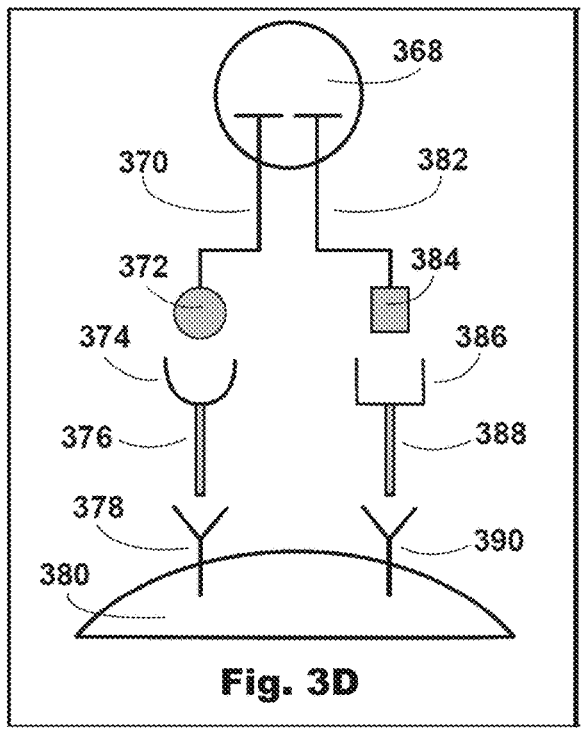

SYSTEM AND METHODS RELATING TO CHIMERIC AUTOANTIBODY RECEPTORS

This application claims the benefit of U.S. Provisional Application Ser. No. 62/873,176, filed Jul. 11, 2019, entitled SYSTEM AND METHODS RELATING TO CHIMERIC AUTOANTIBODY RECEPTORS, the entire disclosure of which is herein incorporated by reference.

FIELD OF THE INVENTION

This invention relates to immunology, autoimmune diseases, chimeric antigen receptors, and chimeric autoantigen receptors.

BACKGROUND OF THE INVENTION

Autoimmune diseases affect about 23.5 million people in the US, and utilize about $100 billion of healthcare resources. Despite their burden on patients, hospitals, and insurance companies, many of these diseases still lack targeted treatments.

Autoimmune diseases are characterized by the presence of immune cells and proteins that react to and destroy healthy cells in the body (and/or the body's own cells), leading to inflammation and tissue injury amongst other conditions. Some antigen-specific therapies are being developed for the treatment of autoimmune disease that are able to target specific components of the immune system that are autoreactive. These autoreactive immune components may be components such as autoantibodies, autoreactive B cells, or autoreactive T cells. In patients with autoimmune disease, autoreactive components target healthy cells by binding to autoantigens or autoantigenic peptides. Some autoreactive components, primarily autoreactive T cells, only bind autoantigenic peptides located on proteins known as major histocompatibility complexes, or MHCs. These MHC-peptide complexes can contain components of autoantigens, but also can contain MHC complex proteins. In humans, MHC proteins are also known as human leukocyte antigen (HLA). MHC can come in different classes, including class I and class II.

Autoantigens are typically self-proteins that are aberrantly targeted in patients with autoimmune disease. Some autoantigens may also be DNA, RNA, carbohydrates, or other biological components that are found inside the patient. Some autoantigenic peptides are presented to the immune system in a complex to MHC. The peptide in an MHC-peptide also does not have to be an autoantigen, and can be derived from foreign substances including bacteria or viruses.

Recent advances have seen the development of adoptive cell therapies that selectively deplete autoreactive immune cells, and they or similar approaches can be used to mitigate or treat autoimmune diseases. Adoptive cell therapy is defined as introducing cells into a patient for therapeutic purposes. Autoreactive immune cells are immune cells that are able to bind to host self-proteins. If autoreactive immune cells bind to self-proteins located on self-cells in the host's body, the autoreactive immune cell may release nonspecific inflammatory molecules and may also produce cytotoxic effects against the self-cells.

T cells receptors (TCRs) are transmembrane receptors that contain an extracellular recognition domain and an intracellular signaling domain. Each T cell expresses TCRs that are able to bind to unique peptides presented by other cells in the body in the context of an MHC complex. TCR binding triggers conformational changes to the signaling domain, which activates the T cell and allows it to kill the cell directly, or recruit other immune cells to kill the cell.

Chimeric antigen receptor (CAR) cells are engineered effector cells that express a CAR construct, which includes an intracellular signaling domain linked to an extracellular antibody-based recognition domain. The recognition domain is engineered to bind to a ligand on a target cell surface. Binding of the recognition domain to its target ligand can activate the signaling domain and activate the effector functions of the effector cell. This can lead to target cell death, anergy, or other changes to the target cell. Current FDA approved treatments using CAR-T cell technology are directed against cancer cells.

Chimeric autoantibody receptor (CAAR) engineered cells are a variation on CAR-T cells that have been engineered to kill autoreactive cells. Traditional CAAR-T cells, described in U.S. Pat. No. 10,301,370, entitled COMPOSITIONS AND METHODS OF CHIMERIC AUTOANTIBODY RECEPTOR T CELLS, the entire disclosure of which is incorporated herein by reference, are transduced T cells genetically engineered to express CAARs that can include an autoantigen or fragment of autoantigen attached to a signaling domain. The signaling domain may include activating domains, such as CD3 or CD28, or inhibitory domains, such as the PD1 endodomain, which can be used to modulate the activity of the engineered cell. The expression of CAARs allow CAAR-T cells to recognize autoreactive cells that bind to the autoantigen. Binding to the autoreactive peptide activates the signaling domain, and if an activation domain is used, the CAAR-T cell will be activated and kill the autoreactive cell. This allows for selective depletion of autoreactive immune cells, and mitigation of the autoimmune disease. Preclinical data using existing CAAR-T cells directed against DSG3, a protein that is targeted by patients with the autoimmune skin disease *Pemphigus vulgaris*, show targeted depletion of autoreactive immune cells in mice.

While traditional CAAR-T cells are useful in complete depletion of B cells for some diseases, they are unable to recognize B cells reactive against several autoantigens made of non-conventional amino acids that arise through post-translational modifications, or nuclear components. Post-translational modifications, such as citrullination or glycosylation, produce amino acids that may be more susceptible to autoimmune recognition. For example, the majority of patients with rheumatoid arthritis, or people who are at high risk of developing rheumatoid arthritis, show elevated levels of anti-citrullinated protein autoantibodies (ACPA). ACPA are directed against proteins containing the amino acid citrulline, which is a post-translational modification of arginine. Traditional methods to create CAARs composed of citrullinated peptides, or other post-translationally modified peptides is challenging because creating conditions necessary to ensure modification of all expressed CAARs is difficult.

Additionally, traditional CAAR-T cells lack flexibility, since they cannot be adjusted for specificity or efficacy once the CAAR has been inserted. Patients with autoimmune diseases often show reactivity towards multiple self-proteins, and to target all of these autoreactive immune cells would require several different CAAR-T cells to be engineered. In some patients, it may also be desirable to delay or turn off the immune system activation, e.g., if the immune system activity is causing side effects or another therapy is to be administered, but this is not possible with traditional CAAR-T cells.

Furthermore, while traditional CAAR-T cells are useful in complete depletion of B cells for some diseases, they are unable to recognize T cells because they do not present autoantigen peptides in complex with MHC. Thus, they can only deplete some disease-associated cells in autoimmune diseases that are mediated by B cells. They are not able to target T cells, which are active in some autoimmune diseases. For example, rheumatoid arthritis and multiple sclerosis are both autoimmune diseases that include a B cell and T cell mediated response. Traditional CAAR-T cells are unable to deplete autoreactive T cells.

SUMMARY OF THE INVENTION

Described herein is an improvement of CAAR technology, which relates to fragmented CAAR systems. In this fragmented CAAR system (the "KIT CAAR" or "fragmented CAAR" described herein), the signaling and recognition portions of the CAAR are separated and present as two different constructs. The recognition construct of the fragmented CAAR system, on its own, can bind to a disease and/or target cell. The signaling construct of the fragmented CAAR system can be expressed by an engineered cell. When activated, the signaling construct of the fragmented CAAR system is able to induce the engineered cell to perform certain effector functions. The signaling construct of the fragmented CAAR system does not bind directly to a disease and/or target cell. The recognition construct and the signaling construct of the fragmented CAAR system each also have a protein binding domain.

As used herein, a "protein interaction domain" or a "protein binding domain" refers to a domain that allows specific binding to other protein(s). A number of exemplary protein interaction domains, as well as pairs of protein interaction domains are provided elsewhere herein.

In the fragmented CAAR system, the recognition and signaling constructs can interact via their respective protein interactions domains. This specific binding can activate the effector functions of the engineered cell in the fragmented CAAR system via the signaling construct and can lead to effector functions against the disease and/or target cell(s) bound by recognition construct(s).

This change in the structure of the CAAR makes the CAAR much more flexible. For instance, if a T cell is altered to have just a signaling portion of the fragmented CAAR and then given to the subject, a physician can provide the recognition portion of the fragmented CAAR as a separate component, allowing the physician to control when and for how long the immune system activates. Additionally, if depletion of a particular autoreactive subset of immune cells turns out to be ineffective or counterproductive, the physician can switch to use of a second recognition construct merely by administering a new recognition component of the CAAR. This is in contrast to traditional CAAR-T, which would require that entirely new CAAR-T cells be engineered and/or force the patient to wait out side effects caused by the original CAAR-T cells.

Additionally, the structure of the fragmented CAAR system ("KIT CAAR") can allow it to recognize cells that express surface molecules that are autoreactive against antigens that are not conventional protein autoantigens, such as those that are post-translationally modified, or those that include carbohydrates or nucleic acids. Depletion of such autoreactive immune cells would play a significant role in the treatment of several autoimmune diseases.

The creation and use of a fragmented CAAR system, described herein, also make it possible to administer complex CAAR-based therapies. For example, the technology described herein, by using multiple recognition molecules, can provide the immune system with instructions to activate if bound by either component 1 or 2. Alternatively, instructions can be provided to the immune system to activate if component 1 (ligand on diseased cell) is recognized, unless component 3 (healthy immune response) is also recognized in the same location. This ability to perform logical computations allows CAAR-T therapy to be adjusted to the needs of individual patients quickly at much lower cost, and in ways that are not possible with traditional CAAR-T therapies.

A variation of the KIT CAAR system relates to chimeric TCR receptor systems. This variation is described herein as the "ChImeric TCR REceptor system" ("CITE system"). In the CITE system, the recognition domain is an MHC-peptide complex, and is present as a separate construct as the signaling domain, which is expressed by the effector cell. The recognition construct of the CITE system, on its own, can bind to a disease and/or target cell, but not activate the effector cell. The signaling construct of the CITE system, on its own, cannot be activated and thus does not induce effector cell-based killing. However, when the recognition and signaling components are present together, they can bind to each other and then function as a complete CITE system.

When the recognition construct is bound to target TCRs as well as the signaling construct expressed by the engineered effector cell, this can lead to activation of the effector cell functions. CITE system engineered effector cell activation can lead to target cell death, anergy of the target cell, or other functions that affect the behavior of the target cell. The split structure of the CITE system also provides it with flexibility. For example, one recognition domain can be easily swapped out for another, or multiple recognition domains can be administered to create logic gates.

Depletion of T cells using the CITE would play a significant role in the treatment of several autoimmune diseases. The creation and use of CITE systems, described herein, also make it possible to administer complex CITE-based therapies. For example, the technology described herein, by using multiple recognition constructs, can provide the immune system with instructions to activate if bound by either construct 1 or 2. Alternatively, instructions can be provided to the immune system to activate if construct 1 (ligand on diseased cell) is recognized unless construct 3 (healthy immune response) is recognized in the same location. This ability to perform logical computations allows CITE system therapy to be adjusted to the needs of individual patients quickly at much lower cost, and in ways that are not possible with traditional CAAR-T therapies.

Additionally, described herein is a variation of the CITE system called the "fused CITE system." The fused CITE system can be a fusion protein that can include a MHC-peptide recognition construct, a transmembrane domain, and a cell signaling domain. This fused CITE system can be expressed by engineered effector cells, and the MHC-peptide recognition construct can be extracellular. The recognition construct could bind to target T cell receptors, and activate the signaling domain of the engineered effector cells. CITE system engineered effector cell activation can lead to target cell death, anergy of the target cell, or other functions that affect the behavior of the target cell.

The MHC-peptide complex of the CITE system and the fused CITE system can be derived from any class of MHC.

In various embodiments, a fragmented chimeric autoantibody receptor system ("fragmented CAAR system") can include a) a first recognition construct including 1) a non-immunoglobulin moiety specific for a first target ligand and 2) a protein binding domain; and b) a signaling construct including 1) an extracellular protein binding domain that can bind specifically with the protein binding domain of the first recognition construct and 2) an intracellular signaling domain.

The protein binding domains can be leucine zipper domains. One leucine zipper domain can be BZip (RR) and the second leucine zipper domain can be AZip (EE).

In various embodiments, the protein binding domains can be PSD95-Dlgl-zo-1 (PDZ) domains.

In various embodiments, one protein binding domain can be streptavidin and a second protein binding domain can be streptavidin binding protein (SBP). In various embodiments, one protein binding domain is FKBP-binding domain of mTOR (FRB) and a second protein binding domain can be FK506 binding protein (FKBP); one protein binding domain can be cyclophilin-Fas fusion protein (CyP-Fas) and a second protein binding domain can be FK506 binding protein (FKBP); one protein binding domain is calcineurin A (CNA) and a second protein binding domain can be FK506 binding protein (FKBP); one protein binding domain can be gibberellin insensitive (GIA) and a second protein binding domain can be gibberellin insensitive dwarf1 (GID1); one protein binding domain can be Snap-tag and a second protein binding domain can be Halo tag; or one protein binding domain can be T14-3-3-cdeltaC and a second protein binding domain can be C-Terminal peptides of PMA2 (CT52).

In various embodiments, one protein binding domain can be pyrabactin resistance-like (PYL) and a second protein binding domain can be ABI. In an embodiment, one protein binding domain can be a nucleotide tag and the second protein binding domain can be a zinc finger domain.

In various embodiments, the protein binding domain of the recognition construct can be a nucleotide tag and the extracellular protein binding domain of the signaling construct can be a zinc finger domain. In an embodiment, the nucleotide tag can be a DNA tag. In an embodiment, the DNA tag can be a dsDNA tag.

In various embodiments, one protein binding domain can be streptavidin and the other protein binding domain can be biotin.

In various embodiments, a non-immunoglobulin moiety can be a moiety based on autoantigen, and can bind to autoreactive receptors. In various embodiments, the non-immunoglobulin moiety can be selected from the group consisting of: affimers, DARpins, aptamers, affibodies, spiegelmers, or autoantigen-based constructs.

In various embodiments, the non-immunoglobulin moiety can include conventional amino acids, non-proteinogenic amino acids including amino acids that have undergone co-translational or post-translational modifications, amino acids that are intermediates in biosynthesis, and synthetic amino acids not found in natural proteins.

In various embodiments, the non-immunoglobulin moiety can contain carbohydrates.

In various embodiments, the non-immunoglobulin moiety can be derived from an MHC-peptide complex or from an MHC-peptide fusion protein.

In various embodiments, the non-immunoglobulin moiety can contain dsDNA, ssDNA, or RNA.

In various embodiments, the non-immunoglobulin moiety can contain a nanoparticle.

In an embodiment, the intracellular signaling domain or TCR signaling domain can contain one or more fragments from a protein selected from the group consisting of: TOIζ, FcRy, FcRp, CD3y, CD35, CD3s, CD3C, CD22, CD79a, CD79b, CD66d, CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), PD1, CD278 (ICOS), DAP10, LAT, KD2C, SLP76, VSIG3/IGSF11, TRIM, ZAP70, and 41BB.

In various embodiments, the signaling construct can be present on the membrane of a cell. In an embodiment, the one or more recognition constructs are present in the extracellular space. In an embodiment, the recognition construct can be bound to the signaling construct by the respective protein binding domains.

In various embodiments, the compositions can further contain a second recognition construct that has 1) a non-immunoglobulin moiety specific for a second target ligand and 2) a protein binding domain that competes with the protein binding domain of the signaling construct for binding to the protein binding domain of the first recognition construct. In an embodiment, the protein binding domain of the second recognition construct and the protein binding domain of the first recognition construct can have a greater affinity than the protein binding domain of the signaling construct and the protein binding domain of the first recognition construct. In an embodiment, the target ligand that can be recognized by the second recognition construct can be found on a healthy and/or non-target cell and not on a diseased and/or target cell.

In various embodiments, the composition can further include a second recognition construct that can include 1) a non-immunoglobulin moiety specific for a second target ligand and 2) a protein binding domain; and the signaling construct further includes a secondary protein binding domain that can specifically bind with the protein binding domain of the second recognition construct. In an embodiment, the affinity of the signaling construct's secondary protein binding domain and the protein binding domain of the second recognition construct can be weaker than the affinity of the signaling construct's first protein binding domain and the protein binding domain of the first recognition construct. In an embodiment, the first and second recognition constructs can each include a secondary protein binding domain; and the secondary protein binding domains can specifically bind to each other.

In various embodiments, described herein can be a composition for a fragmented chimeric autoantibody receptor system (fragmented CAAR system or "KIT CAAR"); the fragmented CAAR can include a) a first recognition construct that can contain 1) a non-immunoglobulin moiety specific for a first target ligand and 2) a first portion of a nucleotide tag; b) a second recognition construct that can contain 1) a moiety specific for a second target ligand and 2) a second portion of the nucleotide tag; and c) a signaling construct that can contain 1) an extracellular zinc finger domain that can bind specifically with a complete nucleotide tag formed by the association of the individual portions of the nucleotide tag and 2) an intracellular signaling domain; wherein the individual portions of the nucleotide tag cannot be specifically bound by the zinc finger domain unless they are associated with each other. In an embodiment, the first portion of the nucleotide tag can be a ssDNA and the second portion of the nucleotide tag can be a complementary ssDNA.

In various embodiments, the composition can further include a third recognition construct which can have 1) a moiety specific for a third target ligand and 2) a third portion of the nucleotide tag; wherein the individual portions or pairwise combinations individual portions of the nucleotide tag cannot be specifically bound by the zinc finger domain, but when all three portions are associated with each other, the resulting complex can be specifically bound by the zinc finger domain. In an embodiment, 1) the first portion of the nucleotide tag can be a ssDNA; and 2) the second and third portions of the nucleotide tag can be ssDNAs, each of which can be complementary to the first portion and 3) the second and third portions of the nucleotide tag have sequences that do not overlap with each other.

In various embodiments, described herein can be a composition including a fragmented chimeric autoantibody receptor (CAAR); the fragmented CAAR including: a) a first recognition construct that can include 1) a non-immunoglobulin moiety specific for a first target ligand and 2) a first nucleotide tag; b) a second recognition construct including 1) a moiety specific for a second target ligand and 2) a second nucleotide tag; and c) a signaling construct including 1) an extracellular zinc finger domain that can bind specifically with the first nucleotide tag and 2) an intracellular signaling domain; wherein the nucleotide tags cannot be specifically bound by the zinc finger domain when they are associated with each other.

In an embodiment, the first nucleotide tag can form a hairpin-loop structure and the second nucleotide tag can be complementary to a portion of the first nucleotide tag that encompasses a portion of one leg of the hairpin-loop and a portion of the loop of the hairpin-loop. In an embodiment, the second target ligand can be found on a healthy and/or non-target cell and not on a diseased and/or target cell.

In various embodiments, a target ligand can be a molecule that can be found on a diseased and/or target cell. In an embodiment, the target ligand specifically bound by a recognition construct that can specifically bind with a signaling construct can be a receptor found on a diseased and/or target cell. In an embodiment, the target ligand, which can be found on a diseased and/or target cell and not on a healthy and/or non-target cell, can be specifically bound by a recognition construct that can also specifically bind with a signaling construct. In various embodiments, the diseased cell can be an autoreactive cell.

In various embodiments, described herein can be a method of killing a target cell, the method including contacting the cell with a composition or cells of any of the foregoing embodiments.

In various embodiments, described herein can be a method of treating a disease, including administering a composition or cells of any of any of the foregoing embodiments to a subject in need of treatment thereof. In an embodiment, the disease can be selected from the group consisting of: autoimmune diseases; atopy; asthma; rheumatoid arthritis; cystic fibrosis; bronchiectasis; type I diabetes; celiac disease; inflammatory bowel disease; multiple sclerosis; vasculitis; Myasthenia gravis; inflammatory diseases; atherosclerosis; Huntington's Disease; Parkinson's Disease; Cardiovascular Disease; infectious disease.

In various embodiments, described herein can be a method of treating autoimmune diseases, including administering a composition or cells of any of the foregoing embodiments to a subject in need of treatment thereof. In an embodiment, the cell can be autologous to the subject.

In an embodiment, the administered cell can be derived and/or descended from a cell obtained from the subject and has been modified ex vivo to include the at least one fragmented CAAR system.

In an embodiment, the administered cell can be derived and/or descended from another patient, a cell line, a stem cell, or an allogenic cell.

In various embodiments, described herein can be an effector cell engineered to express a fragmented chimeric autoantibody receptor (CAAR) signaling construct, wherein the signaling construct can include 1) an extracellular protein binding domain and 2) an intracellular signaling domain. In an embodiment, the protein binding domain can be a leucine zipper domain. In an embodiment, the leucine zipper domain can be BZip (RR) or AZip (EE). In an embodiment, the protein binding domain can be a PSD95-Dlgl-zo-1 (PDZ) domain. In an embodiment, the protein binding domain can be streptavidin, streptavidin binding protein (SBP), or biotin. In an embodiment, the protein binding domain can be FKBP-binding domain of mTOR (FRB) or FK506 binding protein (FKBP). In an embodiment, the protein binding domain can be PYL or ABI. In an embodiment, the protein binding domain can be a nucleotide tag or a zinc finger domain.

In an embodiment, the nucleotide tag can be a DNA tag. In an embodiment, the DNA tag can be a dsDNA tag. In an embodiment, the protein binding domain can be a zinc finger domain. In an embodiment, the signaling construct can be present on the membrane of the cell.

In an embodiment, the cell can be a T cell, NK cell, NKT cell, macrophage, a cell line thereof, other effector cell, off-the-shelf approaches, and stem-cell derived approaches. An off-the-shelf approach can be typically described as an allogenic platform to reduce immune rejection of adoptive cell therapies.

In an embodiment, the intracellular signaling domain can contain one or more fragments from a protein selected from the group consisting of: TCR, FcRy, FcRp, CD3y, CD3δ, CD3s, CD3ζ, CD22, CD79a, CD79b, CD66d, CARD11, CD2, CD7, CD27, CD28, CD30, CD40, CD54 (ICAM), CD83, CD134 (OX40), CD137 (4-1BB), CD 150 (SLAMF1), CD 152 (CTLA4), CD223 (LAG3), CD270 (HVEM), CD273 (PD-L2), CD274 (PD-L1), PD1, CD278 (ICOS), DAPIO, LAT, KD2C, SLP76, TRIM, VSIG3/IGSF11, ZAP70, and 4-1BB. In an embodiment, the signaling construct further includes a secondary protein binding domain that can specifically bind with the protein binding domain of the second recognition construct. In an embodiment, the cell can further include a second fragmented CAAR signaling construct according to any of the embodiments.

In an embodiment, described herein is a method of treating a disease, the method including administering: a cell including a fragmented chimeric autoantibody receptor (CAAR) signaling construct; and a first recognition construct including 1) a non-immunoglobulin moiety specific for a first target ligand and 2) a protein binding domain that can bind specifically with the protein binding domain of the signaling construct; to a subject in need of treatment therefor. In some embodiments, the recognition construct is bound to the signaling construct through their respective protein binding domains prior to usage as a treatment. In some embodiments, separate components of the recognition construct may be assembled prior to any therapeutic action and/or administration. In some embodiments, if multiple recognition constructs are used, they may be bound together prior to any therapeutic action and/or administration. In some embodiments, the non-immunoglobulin moiety can be selected from the group consisting of affimers, DARpins, aptamers, affibodies, spiegelmers, or autoantigen-based constructs. In an embodiment, the non-immunoglobulin moiety can include any combination of conventional amino acids, non-proteinogenic amino acids including amino acids that have undergone co-translational or post-translational modifications, amino acids that are intermediates in biosynthesis, and synthetic amino acids not found in natural proteins.

In an embodiment, the non-immunoglobulin moiety may include carbohydrates. In an embodiment, the non-immunoglobulin moiety may include dsDNA, ssDNA, or RNA. In an embodiment, the non-immunoglobulin can be derived from an MHC-peptide complex or from an MHC-peptide fusion protein. In an embodiment, the cell can be autologous to the subject. In an embodiment, the administered cell can be derived and/or descended from a cell obtained from the subject and has been modified ex vivo to include the at least one fragmented CAAR system. In an embodiment, the protein binding domains are leucine zipper domains. In an embodiment, one leucine zipper domain can be BZip (RR) and the second leucine zipper domain can be AZip (EE). In an embodiment, the protein binding domains are PSD95-Dlgl-zo-1 (PDZ) domains. In an embodiment, one protein binding domain can be streptavidin and a second protein binding domain can be streptavidin binding protein (SBP), or biotin. In an embodiment, one protein binding domain can be FKBP-binding domain of mTOR (FRB) and a second protein binding domain can be FK506 binding protein (FKBP); one protein binding domain can be cyclophilin-Fas fusion protein (CyP-Fas) and a second protein binding domain can be FK506 binding protein (FKBP); one protein binding domain can be calcineurin A (CNA) and a second protein binding domain can be FK506 binding protein (FKBP); one protein binding domain can be gibberellin insensitive (GIA) and a second protein binding domain can be gibberellin insensitive dwarf1 (GID1); one protein binding domain can be Snap-tag and a second protein binding domain can be Halo tag; or one protein binding domain can be T14-3-3-cdeltaC and a second protein binding domain can be C-Terminal peptides of PMA2 (CT52). In an embodiment, when one protein binding domain can be FKBP-binding domain of mTOR (FRB) and a second protein binding domain can be FK506 binding protein (FKBP), the method further includes administering tacrolimus, a rapalog, or everolimus; when one protein binding domain can be cyclophilin-Fas fusion protein (CyP-Fas) and a second protein binding domain can be FK506 binding protein (FKBP), the method further includes administering FKCsA; when one protein binding domain can be calcineurin (CNA) and a second protein binding domain can be FK506 binding protein (FKBP), the method further includes administering FK506; one protein binding domain can be gibberellin insensitive (GIA) and a second protein binding domain can be gibberellin insensitive dwarf1 (GID1), the method further includes administering gibberellin; when one protein binding domain can be Snap-tag and a second protein binding domain can be Halo tag, the method further includes administering HaXS; or when one protein binding domain can be T14-3-3-cdeltaC and a second protein binding domain can be C-Terminal peptides of PMA2 (CT52), the method further includes administering fusicoccin.

In an embodiment, one protein binding domain can be PYL and a second protein binding domain can be ABI. In an embodiment, the protein binding domain of the recognition construct can be a nucleotide tag and the extracellular protein binding domain of the signaling construct can be a zinc finger domain. In an embodiment, the nucleotide tag can be a DNA tag. In an embodiment, the DNA tag can be a dsDNA tag. In various embodiments, the method further includes administering a second recognition construct including 1) a moiety specific for a second target ligand and 2) a protein binding domain that competes with the protein binding domain of the signaling construct for binding to the protein binding domain of the first recognition construct. In an embodiment, the protein binding domain of the second recognition construct and the protein binding domain of the first recognition construct can have a greater affinity than the protein binding domain of the signaling construct and the protein binding domain of the first recognition construct. In an embodiment, the target ligand recognized by the second recognition construct can be found on a healthy and/or non-target cell and not on a diseased and/or target cell.

In various embodiments, the method further can include administering a second recognition construct including 1) a moiety specific for a second target ligand and 2) a protein binding domain; and the signaling construct further includes a secondary protein binding domain that specifically binds with the protein binding domain of the second recognition construct. In an embodiment, the affinity of the signaling construct's secondary protein binding domain and the protein binding domain of the second recognition construct can be weaker than the affinity of the signaling construct's first protein binding domain and the protein binding domain of the first recognition construct. In an embodiment, the first and second recognition constructs each include a secondary protein binding domain; and wherein the secondary protein binding domains specifically bind to each other.

In various embodiments, the method can include administering a) a first recognition construct including 1) a non-immunoglobulin moiety specific for a first target ligand and 2) a first portion of a nucleotide tag; b) a second recognition construct including 1) a moiety specific for a second target ligand and 2) a second portion of the nucleotide tag; wherein the signaling construct includes 1) an extracellular zinc finger domain that can bind specifically with a complete nucleotide tag formed by the association of the individual portions of the nucleotide tag; and wherein the individual portions of the nucleotide tag cannot be specifically bound by the zinc finger domain unless they are associated with each other. In an embodiment, the first portion of the nucleotide tag can be a ssDNA and the second portion of the nucleotide tag can be a complementary ssDNA. In an embodiment, the method can further include administering a third recognition construct which can be 1) a moiety specific for a third target ligand and 2) a third portion of the nucleotide tag; wherein the individual portions or pairwise combinations individual portions of the nucleotide tag cannot be specifically bound by the zinc finger domain, but when all three portions are associated with each other, the resulting complex can be specifically bound by the zinc finger domain. In an embodiment, 1) the first portion of the nucleotide tag can be a ssDNA; and 2) the second and third portions of the nucleotide tag are ssDNAs, each of which can be complementary to the first portion and 3) the second and third portions of the nucleotide tag have sequences that do not overlap with each other.

In various embodiments, the method includes administering: a) a first recognition construct including 1) a non-immunoglobulin moiety specific for a first target ligand and 2) a first nucleotide tag; b) a second recognition construct including 1) a moiety specific for a second target ligand and 2) a second nucleotide tag; wherein the signaling construct includes 1) an extracellular zinc finger domain that can bind specifically with the first nucleotide tag; and wherein the nucleotide tags cannot be specifically bound by the zinc finger domain when they are associated with each other. In an embodiment, the first nucleotide tag forms a hairpin-loop structure and wherein the second nucleotide tag can be complementary to a portion of the first nucleotide tag that encompasses a portion of one leg of the hairpin-loop and a portion of the loop of the hairpin-loop. In an embodiment, the second target ligand can be found on a healthy and/or non-target cell and not on a diseased and/or target cell.

In various embodiments, a target ligand can be a molecule found on a diseased and/or target cell. In an embodiment, the target ligand specifically bound by a recognition construct that can specifically bind with a signaling construct can be a molecule found on a diseased and/or target cell. In an embodiment, the target ligand specifically bound by a recognition construct that can specifically bind with a signaling construct can be a molecule found on a diseased and/or target cell and not on a healthy and/or non-target cell. In an embodiment, the diseased cell can be a cancerous cell.

In various embodiments, the cell can include a second multi-component CAAR signaling construct and the subject can be further administered a second recognition construct including 1) a moiety specific for a second target ligand and 2) a protein binding domain that can bind specifically with the protein binding domain of the second signaling construct. In an embodiment, the intracellular signaling domain of the second fragmented CAAR signaling construct inhibits effector cell activity. In an embodiment, the target ligand specifically bound by a recognition construct that can specifically bind with the second signaling construct can be a ligand found on a healthy and/or non-target cell. In an embodiment, the target ligand specifically bound by a recognition construct that can specifically bind with the second signaling construct is a ligand found on a healthy and/or non-target cell and not on a diseased and/or target cell.

In various embodiments, a fragmented chimeric autoantibody receptor (KIT CAAR) can include at least one recognition construct including 1) a non-immunoglobulin moiety and 2) a recognition protein binding domain, and at least one cell engineered to express at least one signaling construct including 1) an intracellular cell signaling domain and 2) a signaling protein binding domain that can bind to the protein binding domain of at least one of the at least one recognition construct.

In various embodiments, the non-immunoglobulin moiety can bind to a target ligand found on a target cell associated with a medical condition selected from the group consisting of: autoimmune diseases, atopy, rheumatoid arthritis, cystic fibrosis, bronchiectasis, type I diabetes, celiac disease, inflammatory bowel disease, multiple sclerosis, autoimmunity, autoimmune response, vasculitis, myasthenia gravis, inflammatory diseases, inflammation, inflammatory response, neurological diseases, including Huntington's disease and Parkinson's disease, cardiovascular disease, including atherosclerosis, and infectious disease. The non-immunoglobulin moiety can be selected from the group consisting of: affimers, DARPins, aptamers, affibodies, spiegelmers, autoantigen, MHC-autoantigen, MHC fragment, complexed MHC-autoantigen, complexed MHC fragment, MHC-peptide, complexed MHC-peptide, fused MHC-peptide, autoantigen fragment, autoantigen-based constructs, sugar-based constructs, and lipid-based constructs. The intracellular signaling domain can be activated only when at least one of the at least one recognition constructs can be bound to both the target ligand and the signaling protein binding domain of at least one of the at least one signaling constructs. The intracellular signaling domain may activate or inhibit effector functions of the cell. The cell can be selected from the group consisting of: T cells, NK cells, NKT cells, Treg, macrophages, a cell line, other effector cells, allogenic cells, autologous cells, and stem-cell derivatives. At least one of the at least one recognition constructs and at least one of the at least one signaling constructs can be used to make at least one logic gate. The cell can be further engineered to express at least one chimeric antigen receptor.

In various embodiments, a fused chimeric TCR engager (CITE) system can include an MHC-peptide complex, a transmembrane domain, and an intracellular cell signaling domain.

In various embodiments, a method of administering a KIT CAAR system to a patient can include obtaining cells, engineering the cells into engineered cells that express at least one signaling construct of the KIT CAAR system, and inserting the engineered cells into the patient.

In various embodiments, the method can include inserting at least one recognition construct into the patient. Inserting the engineered cells into the patient and inserting the at least one recognition construct into the patient can include a delivery method selected from the group consisting of: through mucosal membranes, intravenously, topically, by joint injections, orally, by intramuscular injection, by subcutaneous injection, and by intrathecal therapy The method can include administrating additional treatments or procedures. Obtaining cells can include obtaining the cells from the patient or modifying the cells ex vivo. Inserting the engineered cells into the patient can include inserting engineered cells that can be allogenic cells or inserting engineered cells that can be autologous cells. Inserting the engineered cells in to the patient can include inserting the engineered cells into the patient to treat a medical condition that can be selected from the group consisting oft autoimmune diseases, atopy, rheumatoid arthritis, cystic fibrosis, bronchiectasis, type I diabetes, celiac disease, inflammatory bowel disease, multiple sclerosis, autoimmune response, vasculitis, Myasthenia gravis, inflammatory diseases, inflammation, inflammatory response, neurological diseases, including Huntington's disease and Parkinson's disease, cardiovascular disease, including atherosclerosis, and infectious disease The method can include using the method in a profitable manner. Inserting at least one recognition construct can further include inserting at least a first recognition construct and a second recognition construct. Engineering the engineered cells can include engineering the engineered cells to express at least a first signaling construct and a second signaling construct. Engineering the engineered cells can include engineering the engineered cells to express at least a first signaling construct and a second signaling construct, and wherein the engineered cells can include multiple groups of engineered cells, and wherein each group of engineered cells can express a different signaling construct of the at least the first signaling construct and the second signaling construct.

BRIEF DESCRIPTION OF THE DRAWINGS

FIG. 3A is a schematic view of a fragmented CAAR system demonstrating how the fragmented CAAR system can be used for logic computation to create an activating "and" gate, according to an illustrative embodiment;

FIG. 3B is a schematic view of a fragmented CAAR system demonstrating how the fragmented CAAR system can be used for logic computation to create an inhibitory "and" gate, according to an illustrative embodiment;

FIG. 3C is a schematic view of a fragmented CAAR system demonstrating how the fragmented CAAR system can be used for logic computation to create an activating "or" gate, according to an illustrative embodiment;

FIG. 3D is a schematic view of a fragmented CAAR system demonstrating how the fragmented CAAR system can be used for logic computation to create an inhibitory "or" gate, according to an illustrative embodiment;

DETAILED DESCRIPTION

Figure 1A:
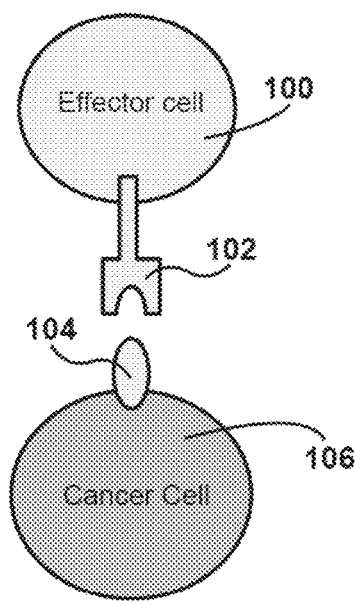
FIG. 1A is a schematic view of conventional chimeric antigen receptor (CAR) technology, according to an illustrative embodiment.

The following detailed descriptions will be better understood when read in conjunction with the appended drawings. It should be understood, however, that the system and methods described herein are not limited to the precise arrangements and instrumentalities of the embodiments shown in the drawings.

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element. The numerical terms "first," "second," and so on are used herein to refer to the order in which components are described and do not limit relevant construct to only one, two, or any other specific quantities of the components being described.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times greater, at least 50 times greater, at least 100 times greater, at least 500 times greater, at least 1000 times greater, or greater, than the affinity for the third nontarget entity. A reagent specific for a given target is one that exhibits specific binding for that target under the conditions of the assay being utilized.

Traditional CARs are fusion proteins made up of a recognition domain and a signaling domain that are expressed by engineered effector cells. The recognition domain is derived from an immunoglobulin that is specific for a target ligand on a target cell. This recognition domain allows the effector cell to bind to the target, which can activate the signaling domain. This can allow the effector cell to kill the target cell, inhibit its growth, or affect the target cell's behavior in some other manner. Traditional CAR recognition domains are limited to immunoglobulin-derived domains that are difficult to engineer for targeting specific autoreactive T cells. Autoreactive T cells are T cells that express T cell receptors (TCRs) directed against self-antigen, and are implicated in autoimmune and inflammatory diseases. TCRs bind only to peptides that are presented by MHC-peptide complexes. There are multiple classes of MHC, and some TCRs preferentially bind one class over another. Traditional CAR recognition domains, being immunoglobulin based and not MHC-peptide based, would be extremely difficult to engineer to target TCRs and act on autoreactive T cells.

Traditional CAARs are fusion proteins made up of a recognition domain and a signaling domain that are expressed by engineered effector cells. The recognition domain is derived from a protein autoantigen and allows the effector cell to bind to receptors expressed on autoreactive immune cells. The binding activates the signaling domain, allowing the effector cell to kill the autoreactive immune cell as a treatment for autoimmune diseases. Traditional CAAR recognition domains are limited to peptides that can be expressed by the effector cell, a significant barrier to applying CAAR technology towards autoimmune diseases that produce autoantibodies against non-conventional autoantigens, such as those that are post-translationally modified.

Described herein are the components of a fragmented CAAR system ("KIT CAAR"), which can include recognition constructs and the signaling constructs that are separate entities capable of interaction via complementary protein interactions domains. A "recognition construct" can be an autoantigen-based reagent that can include 1) a non-immunoglobulin moiety, and 2) a protein binding domain. A variation of the KIT CAAR system relates to chimeric TCR receptor systems. This variation is described herein as the "ChImeric TCR REceptor system" ("CITE system"). In the case of a CITE system, the non-immunoglobulin moiety of the recognition construct can be an MHC-peptide complex (and/or fragment thereof). The MHC-peptide complex may be a fusion protein of MHC and peptide. The MHC-peptide complex of a CITE system can be engineered to specifically target a TCR. The target TCR can be a TCR directed against self-antigen(s). This modular structure of the KIT CAAR can allow for recognition constructs derived from autoantigens and MHC-peptide to be easily constructed and administered. Additionally, the modular platform allows for the delivery of more than one CAAR, allowing for complex logic computations and more precise control over CAAR-based immunotherapy.

Also described are effector cells that have been engineered to express one or more components of the fragmented CAAR system, including the CITE system variation and the fused CITE system variation (described more fully below). In various embodiments, the engineered effector cell can have high affinity for a CAAR system recognition domain, which can bind to autoantibodies expressed on B cells. This engineered effector cell can be activated by CAAR system recognition domain bound to its target and induce killing of these B cells. In various embodiments, the engineered effector cell can interact with a CITE system recognition domain, which can interact with a target TCR. This engineered effector cell be activated by recognition domain and induce killing of T cells expressing the target TCR. In yet another embodiment, the cell can have low affinity for antibodies bound to a Fc receptor, to minimize toxicity against non-autoreactive cells.

Also described is a variation of the CITE system, which can be a fusion protein that can include a signaling domain, transmembrane domain, and recognition domain. This variation is described as a "fused CITE system." The recognition domain of the fusion protein in the fused CITE system can be based on an MHC-peptide complex or MHC-peptide fusion protein. The fused CITE system recognition domain can be engineered to bind specifically to a target TCR, which can be a TCR directed against self-antigen. Binding of the fused CITE system recognition domain can activate the fused CITE system signaling domain.

Also described are effector cells that have been engineered to express one or more fused CITE systems. In various embodiments, this engineered effector cell can interact with a target TCR and induce its effector functions selectively against T cells expressing the target TCR.

The systems and methods described herein also relates to the use of a fragmented CAAR system, CITE system, and/or fused CITE system in the treatment or diagnosis of diseases related to the expression of an autoimmune response, which is an immune response against the body's own cells. Cells expressing components of a fragmented CAAR system are able to distinguish and kill autoreactive cells while leaving non-target cells intact. In some embodiments, this approach can be applied to treat or diagnose or recognize infectious disease(s).

FIG. 1 is an illustration depicting various embodiments of engineered immune cells, and the fragmented CAAR technology described herein. FIG. 1A shows an example of conventional chimeric antigen receptor (CAR) technology. Effector cell 100 has been modified to express CAR 102, which can be a polypeptide including an antibody-derived ectodomain fused to an intracellular cell signaling domain. The antibody-derived ectodomain of CAR 102 can bind to target ligand 104, which can be expressed on cancer cell 106. This binding activates the intracellular cell signaling domain of CAR 102, causing effector cell 100 to release cytotoxic chemicals to kill cancer cell 106.

Figure 1B:
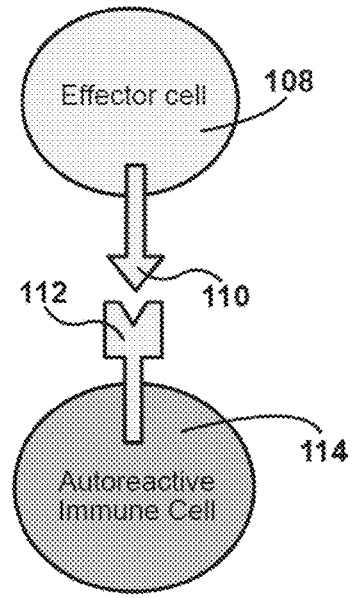
FIG. 1B is a schematic view of a conventional chimeric autoantibody receptor (CAAR) technology, according to an illustrative embodiment.

FIG. 1B shows an example of conventional chimeric autoantibody receptor (CAAR) technology. Effector T cell 108 has been modified to express CAAR 110, which can be a polypeptide with an extracellular autoantigen-derived domain fused to an intracellular cell signaling domain. The extracellular autoantigen-derived domain of CAAR 110 can bind to autoreactive receptor 112, which can be expressed on autoreactive immune cell 114. This binding activates the intracellular cell signaling domain of CAAR 110, causing effector cell 108 to release cytotoxic chemicals to kill autoreactive immune cell 114.

Figure 1C:
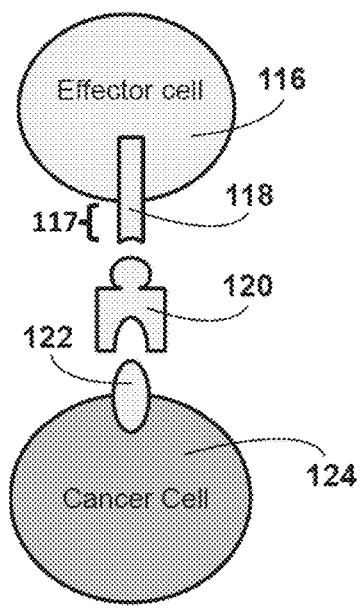
FIG. 1C is a schematic view of multi-component (SUPRA) CAR technology, according to an illustrative embodiment.

FIG. 1C shows an example of multi-component (SUPRA) CAR technology. Effector cell 116 has been modified to express a signaling construct 118, which can include an intracellular cell signaling domain and an extracellular protein binding domain. The extracellular protein binding domain 117 of signaling polypeptide 118 can bind to recognition polypeptide 120. The recognition polypeptide 120 can contain 1) an antibody-based reagent and 2) a protein binding domain that interacts with the protein binding domain of signaling polypeptide 118. The antibody-based reagent of the recognition polypeptide 120 specifically binds to target ligand 122 on cancer cell 124. The effector cell 116 can be activated when recognition polypeptide 120 binds to both signaling polypeptide 118 and target ligand 122.

Figure 1D:
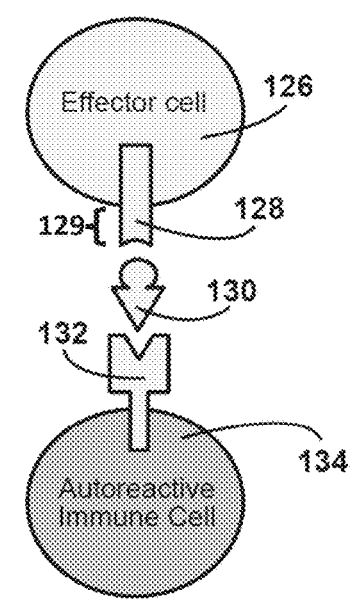
FIG. 1D is a schematic view of a fragmented chimeric autoantibody receptor (CAAR) technology, according to an illustrative embodiment.

FIG. 1D shows an example of a fragmented CAAR system, according to an illustrative embodiment. Effector cell 126 has been modified to express a signaling polypeptide 128, which can include an intracellular cell signaling domain and an extracellular protein binding domain. The extracellular protein binding domain 129 of signaling polypeptide 128 can bind to recognition construct 130. The recognition construct 130 can include 1) a non-immunoglobulin moiety and 2) a protein binding domain that interacts with the protein binding domain of signaling polypeptide 128. The non-immunoglobulin moiety of the recognition construct 130 specifically binds to autoreactive receptor 132 on autoreactive immune cell 134. The effector cell 126 can be activated when recognition construct 130 is bound to both signaling construct 128 and autoreactive receptor 132.

In various embodiments, the example of the fragmented CAAR depicted in FIG. 1D can be of the CITE system variety. In an example of a CITE system, the non-immunoglobulin moiety of recognition construct 130 can be an MHC-peptide complex (and/or fragment thereof). The MHC-peptide of the recognition construct 130 can specifically bind to autoreactive receptor 132 on autoreactive immune cell 134. Autoreactive immune cell 134 can be a T cell. Autoreactive receptor 132 can be a TCR.

In the case of a CITE system, the non-immunoglobulin moiety of the recognition construct can be an MHC-peptide complex (and/or fragment thereof). The MHC-peptide complex may be a fusion protein of MHC and peptide. The MHC-peptide complex of a CITE system can be engineered to specifically target a TCR. The target TCR can be a TCR directed against self-antigen(s). This modular structure of the KIT CAAR can allow for recognition constructs derived from autoantigens and MHC-peptide to be easily constructed and administered. Additionally, the modular platform allows for the delivery of more than one CAAR, allowing for complex logic computations and more precise control over CAAR-based immunotherapy. The recognition construct of the CITE system, on its own, can bind to a disease and/or target cell, but not activate the effector cell. The signaling construct of the CITE system, on its own, cannot be activated and thus does not induce effector cell-based killing. However, when the recognition and signaling components are present together, they can bind to each other and then function as a complete CITE system. When the recognition construct is bound to target TCRs as well as the signaling construct expressed by the engineered effector cell, this can lead to activation of the effector cell functions. CITE system engineered effector cell activation can lead to target cell death, anergy of the target cell, or other functions that affect the behavior of the target cell. The split structure of the CITE system also provides it with flexibility. For example, one recognition domain can be easily swapped out for another, or multiple recognition domains can be administered to create logic gates. Depletion of T cells using the CITE would play a significant role in the treatment of several autoimmune diseases. The creation and use of CITE systems, described herein, also make it possible to administer complex CITE-based therapies. For example, the technology described herein, by using multiple recognition constructs, can provide the immune system with instructions to activate if bound by either construct 1 or 2. Alternatively, instructions can be provided to the immune system to activate if construct 1 (ligand on diseased cell) is recognized unless construct 3 (healthy immune response) is recognized in the same location. This ability to perform logical computations allows CITE system therapy to be adjusted to the needs of individual patients quickly at much lower cost, and in ways that are not possible with traditional CAAR-T therapies. The MHC-peptide complex of the CITE system and the fused CITE system can be derived from any class of MHC. In an embodiment, a cell engineered with a KIT CAAR system can be further engineered to express at least one chimeric antigen receptor. In an embodiment, an intracellular signaling domain of a KIT CAAR system may activate or inhibit effector functions of the cell.

Figure 2:
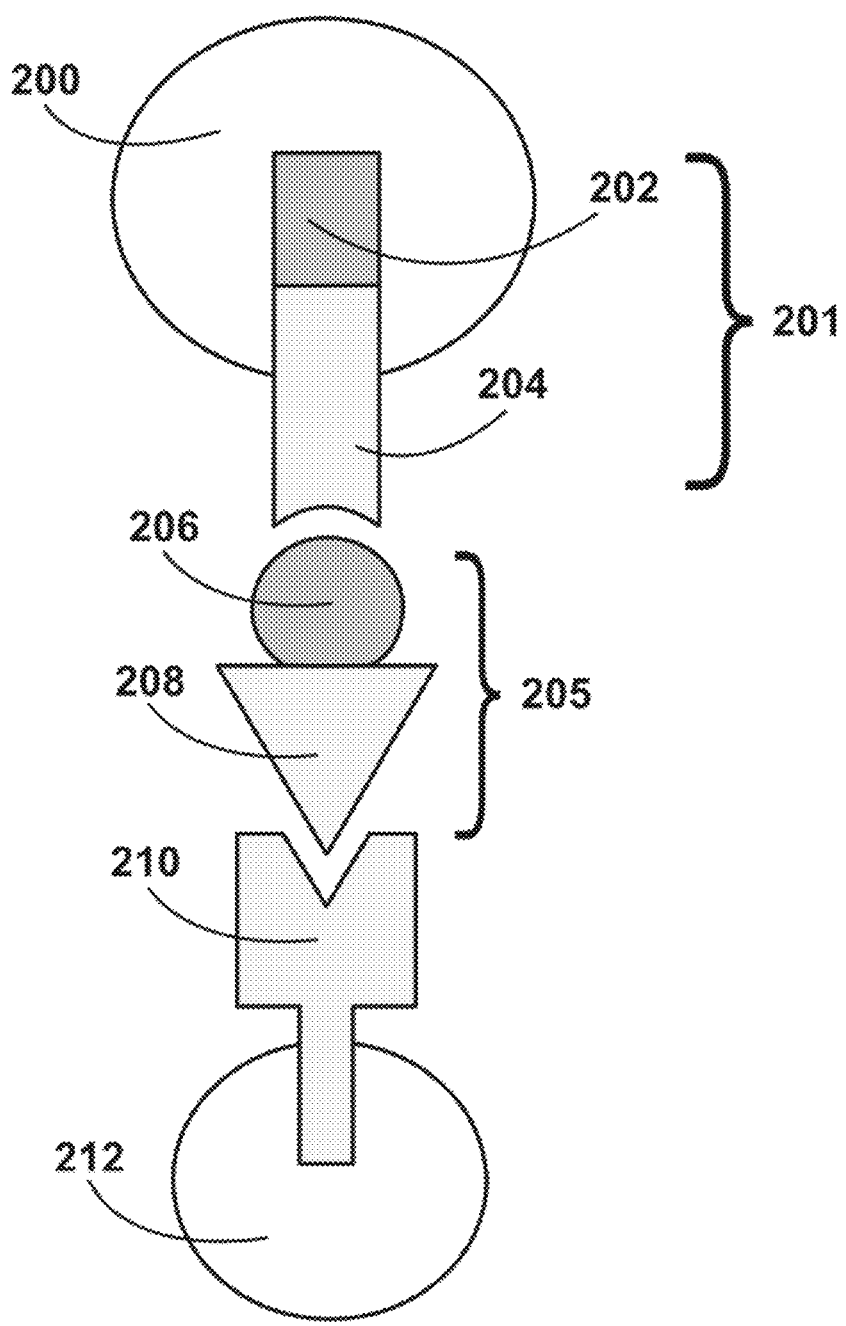
FIG. 2 is a schematic view of the components of the fragmented CAAR system ("KIT CAAR"), according to an illustrative embodiment.

FIG. 2 is a schematic drawing of the components making up a potential fragmented CAAR described herein. The transmembrane signaling construct of the fragmented CAAR can be expressed by effector cell 200. The signaling construct 201 can include intracellular cell signaling domain 202 and signaling construct protein binding domain 204. In various embodiments, intracellular cell signaling domain 202 can be connected to the signaling construct protein binding domain 204 via a linker region. In various embodiments, this linker region can cross into or span the membrane.

The fragmented CAAR can also contain a recognition construct 205 that can include recognition construct protein binding domain 206, and non-immunoglobulin moiety 208. In various embodiments, the recognition construct can be a fusion protein. In various embodiments, the recognition construct protein binding domain 206 of the recognition construct is chemically crosslinked to recognition domain 208. Recognition construct protein binding domain 206 is capable of binding to signaling construct protein binding domain 204. Non-immunoglobulin moiety 208 can bind to autoreactive receptor 210. Autoreactive receptor 210 can be located on the membrane of autoreactive immune cell 212. Binding of signaling construct protein binding domain 204 to recognition construct protein binding domain 206 in conjunction with binding of non-immunoglobulin moiety 208 to autoreactive receptor 210 can activate the cell signaling domain 202. Autoreactive receptor 210 can be an autoreactive TCR and/or autoreactive BCR. Activation of the cell signaling domain 202 can trigger effector functions of effector cell 200 against the autoreactive immune cell 212. In various embodiments, these effector functions can include the release of cytotoxic chemicals, phagocytosis, induction of anergy, and inhibition of the effector cell. In various embodiments, effector cell 200 can also be engineered to express a chimeric antigen receptor along with the signaling construct. The chimeric antigen receptor can bind to cytokines and reduce inflammation. In various embodiments, effector cell 200 can be engineered with a suicide switch to induce autophagy if bound to a particular ligand.

The effector cell 200 can be selected from any of the following: T cells, NK cell, NKT cell, macrophage, Treg, a cell line thereof, other effector cell, off-the-shelf approaches, and stem-cell derived approaches.

In various embodiments, the intracellular cell signaling domain 202 can contain domains derived from one or more proteins selected from the group consisting of: TCRC, FcRy, FcRp, CD3y, CD3δ, CD3s, CD247 (CD3-zeta), CD3C, CD22, CD79a, CD79b, CD66d, CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), PD1, CTLA4, CD278 (ICOS), CD279 (PD1), DAP10, LAT, KD2C, SLP76, TRIM, ZAP70, and 41BB.

In various embodiments, the intracellular cell signaling domain 202 can be a "first generation" CAR signaling domain, which is derived from CD247 (CD3-zeta).

In various embodiments, the intracellular cell signaling domain 202 can be a "second generation" CAR signaling domain, which can contain a costimulatory domain in addition to CD3-zeta. The costimulatory signaling domain can be derived from receptors including CD28, 4-1BB, PD-1, CTLA-4, DAP10, OX40, and/or ICOS.

In various embodiments, the signaling construct protein binding domains 204 can be selected from the group consisting of: leucine zipper domain BZip (RR), leucine zipper domain AZip (EE), PSD95-Dlgl-zo-1 (PDZ) domain, streptavidin, streptavidin binding protein (SBP), biotin, FKBP-binding domain of mTOR (FRB), FK506 binding protein (FKBP), cyclophilin-Fas fusion protein (CyP-Fas), FK506 binding protein (FKBP), calcineurinA (CNA), gibberellin insensitive (GIA), gibberellin insensitive dwarf 1 (GID1), Snap-tag, Halo tag, T14-3-3-cdeltaC, C-Terminal peptides of PMA2 (CT52), PYL, and ABI.

In various embodiments, the recognition construct protein binding domain 206 can be selected from the group consisting of: leucine zipper domain BZip (RR), leucine zipper domain AZip (EE), PSD95-Dlgl-zo-1 (PDZ) domain, streptavidin, streptavidin binding protein (SBP), biotin, FKBP-binding domain of mTOR (FRB), FK506 binding protein (FKBP), cyclophilin-Fas fusion protein (CyP-Fas), FK506 binding protein (FKBP), calcineurinA (CNA), gibberellin insensitive (GIA), gibberellin insensitive dwarf 1 (GID1), Snap-tag, Halo tag, T14-3-3-cdeltaC, C-Terminal peptides of PMA2 (CT52), PYL, and ABI.

In various embodiments, the signaling construct protein binding domain 204 or recognition construct binding domain 206 can be a zinc finger domain, and the other can be a nucleotide tag that can include dsDNA.

In various embodiments, the non-immunoglobulin moiety 208 can be any of the following (and/or fragments thereof): affimers, DARPins, aptamers, affibodies, spiegelmers, autoantigen, MHC-autoantigen, MHC fragment, complexed MHC-autoantigen, complexed MHC fragment, MHC-peptide, complexed MHC-peptide, fused MHC-peptide, and/or autoantigen-based construct.

In various embodiments, the non-immunoglobulin moiety 208 can be constructed from any combination of the following: conventional amino acids, non-proteinogenic amino acids including amino acids that have undergone co-translational or post-translational modifications, amino acids that are intermediates in biosynthesis, synthetic amino acids not found in natural proteins, carbohydrates, nanoparticles, ribonucleoproteins, lipids, dsDNA, ssDNA, and RNA. In various embodiments, the non-immunoglobulin moiety 208 of recognition construct 205 can be an MHC-peptide complex or derived from an MHC-peptide complex. In various embodiments, the non-immunoglobulin moiety 208 of recognition construct 205 can be an autoantigen or derived from an autoantigen. In various embodiments, recognition construct 205 and/or non-immunoglobulin moiety 208 can bind to target cell(s) such as autoimmune cell(s), autoreactive cell(s), inflammatory cell(s), autoimmune T-cell(s), autoimmune B-cell(s), plasma cell(s), and/or autoimmune plasma cell(s). A target ligand can be a ligand indicative of a target cell(s). A target ligand can be a ligand found on a diseased and/or target cell. The KIT CAAR can be referred to as a CITE system if the non-immunoglobulin moiety of recognition construct 208 can be an MHC-peptide complex or derived from an MHC-peptide complex.

FIGS. 3A-3D are schematic diagrams depicting examples of logic gates that can be created using different recognition constructs and signaling constructs of a fragmented CAAR system.

FIG. 3A is a schematic diagram depicting an example of an activating "and" gate. In FIG. 3A, the effector cell 300 expresses a CAAR signaling construct including a signaling domain 302 and two protein binding domains: 304 and 306. The first protein binding domain 304 binds specifically to protein binding domain 308 on a first recognition construct. This first recognition construct can further contain a non-immunoglobulin moiety 310, which binds to receptor 312 expressed by autoreactive cell 314.

The second protein binding domain 306 binds specifically to protein binding domain 316 on a second recognition construct. This second recognition construct can further include a non-immunoglobulin moiety 318, which binds to a receptor 320 also expressed by autoreactive cell 314. Activation of signaling domain 302 will only occur if all of the following are bound: receptor 312 to non-immunoglobulin moiety 310, protein binding domain 308 to protein binding domain 304, receptor 320 to non-immunoglobulin moiety 318, and protein binding domain 316 to protein binding domain 306. Activation of signaling domain 302 will activate the functions of effector cell 300 against autoimmune cell 314.

In various embodiments, non-immunoglobulin moiety 310 and/or non-immunoglobulin moiety 318 can each be an MHC-peptide complex or derived from an MHC-peptide complex. The KIT CAAR can be referred to as a CITE system if non-immunoglobulin moiety 310 and/or non-immunoglobulin moiety 318 are MHC-peptide complexes or derived from MHC-peptide complexes.

FIG. 3B is a schematic diagram depicting an example of an inhibitory "and" gate. In FIG. 3B, the effector cell 322 expresses a CAAR signaling construct including a signaling domain 324 and two protein binding domains: 326 and 328. The first protein binding domain 326 binds specifically to protein binding domain 330 on a first recognition construct. This first recognition construct can further include non-immunoglobulin moiety 332, which binds to receptor 334 expressed by healthy cell 336.

The second protein binding domain 328 binds specifically to protein binding domain 338 on a second recognition construct. This second recognition construct can further include non-immunoglobulin moiety 340 which binds to receptor 342, which can also expressed by healthy cell 336. Activation of signaling domain 324 will only occur if all of the following are bound: receptor 334 to non-immunoglobulin moiety 332, protein binding domain 330 to protein binding domain 326, receptor 342 to non-immunoglobulin moiety 340, and protein binding domain 338 to protein binding domain 328. Activation of signaling domain 324 will inhibit the functions of effector cell 322.

In various embodiments, non-immunoglobulin moiety 332 and/or non-immunoglobulin moiety 340 can each be an MHC-peptide complex or derived from an MHC-peptide complex. The KIT CAAR can be referred to as a CITE system if non-immunoglobulin moiety 332 and/or non-immunoglobulin moiety 340 are MHC-peptide complexes or derived from MHC-peptide complexes.

FIG. 3C is a schematic diagram depicting an example of an activating "or" gate. In FIG. 3C, the effector cell 344 expresses two CAAR signaling constructs. The first signaling construct can contain signaling domain 346 and protein binding domain 348. Protein binding domain 348 binds specifically to protein binding domain 350 on a first recognition construct. The first recognition construct further contains non-immunoglobulin moiety 352 which binds to receptor 354 expressed by autoreactive cell 356. Binding of receptor 354 to non-immunoglobulin moiety 352 in conjunction with binding of protein binding domain 350 to protein binding domain 348 will activate signaling domain 346.

The second signaling construct can include signaling domain 358 and protein binding domain 360. Protein binding domain 360 binds specifically to protein binding domain 362 on a first recognition construct. The first recognition construct can contain non-immunoglobulin moiety 364, which can bind to receptor 366 expressed by autoreactive cell 356. Binding of receptor 366 to non-immunoglobulin moiety 364 in conjunction with binding of protein binding domain 362 to protein binding domain 360 can activate signaling domain 358.

Activation of either signaling domain 346 or signaling domain 358 can activate the functions of effector cell 344.

In various embodiments, non-immunoglobulin moiety 352 and/or non-immunoglobulin moiety 364 can each be an MHC-peptide complex or derived from an MHC-peptide complex. The KIT CAAR can be referred to as a CITE system if non-immunoglobulin moiety 352 and/or non-immunoglobulin moiety 364 are MHC-peptide complexes or derived from MHC-peptide complexes.

FIG. 3D is a schematic diagram depicting an example of an inhibitory "or" gate. In FIG. 3D, the effector cell 368 expresses two CAAR signaling constructs. The first signaling construct can include signaling domain 370 and protein binding domain 372. Protein binding domain 372 binds specifically to protein binding domain 374 on a first recognition construct. The first recognition construct can further include non-immunoglobulin moiety 376 which binds to receptor 378 expressed by healthy cell 380. Binding of receptor 378 to non-immunoglobulin moiety 376 in conjunction with binding of protein binding domain 374 to protein binding domain 372 will activate signaling domain 370.

The second signaling construct can include signaling domain 382 and protein binding domain 384. Protein binding domain 384 can bind specifically to protein binding domain 386 on a first recognition construct. The first recognition construct can include non-immunoglobulin moiety 388 which binds to receptor 390, also expressed by healthy cell 380. Binding of receptor 390 to non-immunoglobulin moiety 388 in conjunction with binding of protein binding domain 386 to protein binding domain 384 will activate signaling domain 382.

Activation of either signaling domain 370 or signaling domain 382 will inhibit the functions of effector cell 368.

In various embodiments, non-immunoglobulin moiety 376 and/or non-immunoglobulin moiety 388 can each be an MHC-peptide complex or derived from an MHC-peptide complex. The KIT CAAR can be referred to as a CITE system if non-immunoglobulin moiety 376 and/or non-immunoglobulin moiety 388 are MHC-peptide complexes or derived from MHC-peptide complexes.

Figure 4:
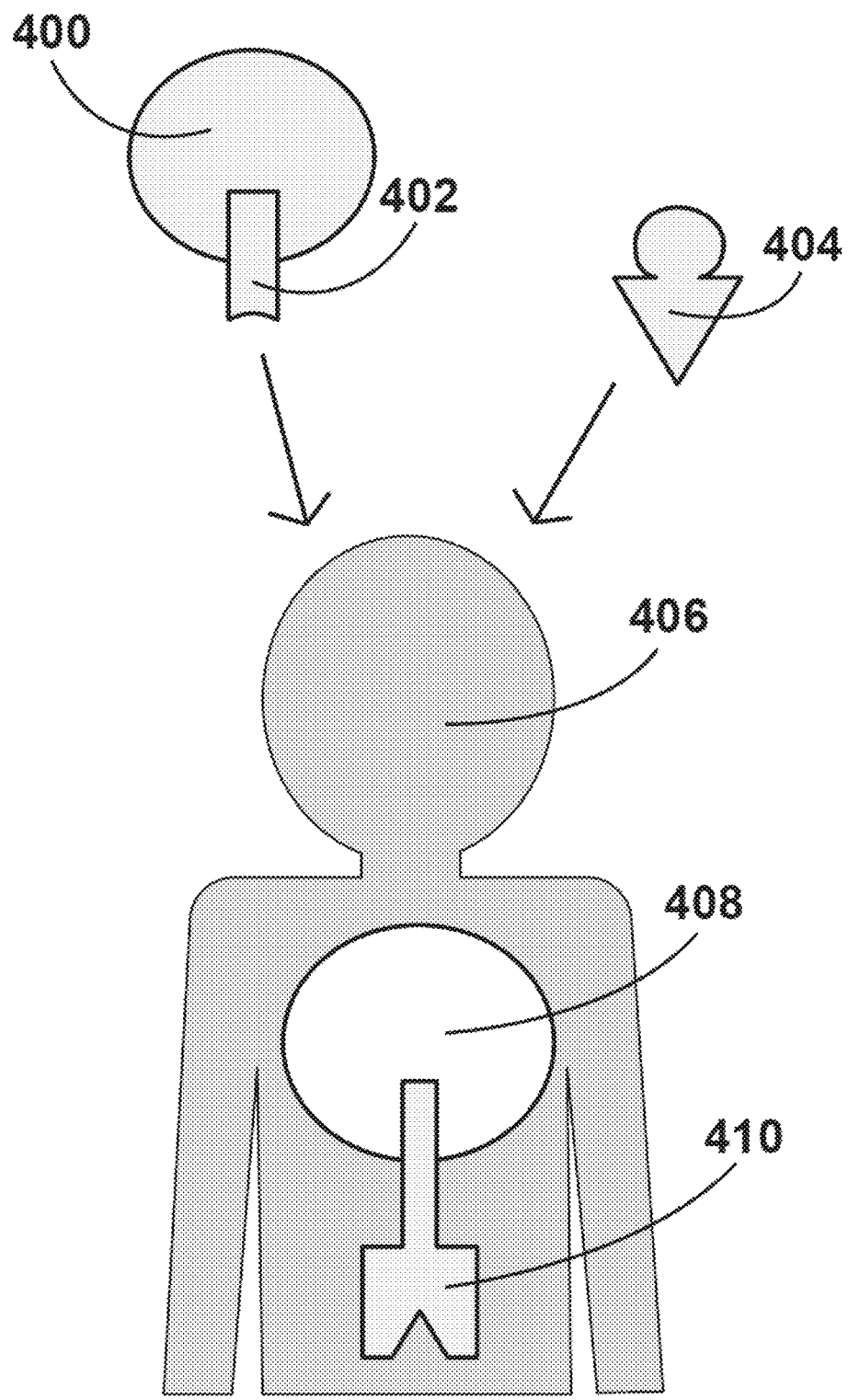
FIG. 4 is a schematic view of a fragmented CAAR system depicting an example of a method of use of a fragmented CAAR system, according to an illustrative embodiment.

FIG. 4 describes an embodiment(s) of the methods of use of a fragmented CAAR system. Effector cell 400 has been engineered to express signaling construct 402, which binds to recognition construct 404. Effector cell 400 and recognition construct 404 are administered to patient 406 in appropriate doses to produce therapeutic effects. Effector cell 400 and recognition construct 404 may administered in separate doses or together as one dose. Target cell 408 can be found in patient 406 and can express autoreactive receptor 410. Autoreactive receptor 410 can specifically bind to the non-immunoglobulin moiety present on recognition construct 404. Only binding of autoreactive receptor 410 to recognition construct 404 in conjunction with binding of recognition construct 404 to signaling construct 402 activates the functions of effector cell 400. Activation of effector cell 400 leads to the cell death of target cell 408 to produce therapeutic effects.

In various embodiments, the effector cell may be derived from patient 406, another person, stem cells, off-the-shelf approaches, or a cell line.

In various embodiments, effector cell 400 and recognition construct 404 may be administered intravenously, through mucosal membranes, topically, by joint injections, orally, by intramuscular injection, by subcutaneous injection, or by intrathecal therapy.

In various embodiments, effector cell 400 and recognition construct 404 are administered in conjunction with or following other medical treatments. In various embodiments, additional treatments and/or procedures can include medical treatments, diagnostic procedures, chemotherapy, autoimmune treatment, lymphodepletion, biologics, small molecules, radiation therapy, medical procedures, erythropoietin, etc.

In various embodiments, target cell 408 contributes to the symptoms of any of the following condition and/or diseases: autoimmune diseases, atopy, rheumatoid arthritis, cystic fibrosis, bronchiectasis, type I diabetes, celiac disease, inflammatory bowel disease, multiple sclerosis, vasculitis, autoimmunity, inflammation, Myasthenia gravis, inflammatory diseases, atherosclerosis, Huntington's Disease, Parkinson's Disease, Cardiovascular Disease, and infectious disease.

The KIT CAAR approach is distinct and unique from existing multi-component CAR approaches, including split and/or universal approaches, because the recognition domain in the KIT CAAR approach is not immunoglobulin based. Instead, the KIT CAAR recognition domain can be used to bind to receptors on autoreactive cells, instead of ligands on cancer cells. The KIT CAAR approach can be used for autoimmune diseases and related conditions, not cancer. Another important factor to consider is that the KIT CAAR factors in the use of ancillary technologies or methods for treatment purposes. These described distinctions are only some of the differences between KIT CAAR and other CAR approaches.

Furthermore, the KIT CAAR cell can be more flexible compared to a conventional CAAR because the signaling construct and the recognition construct of a KIT CAAR are separate components. This can allow for the delivery of several different recognition constructs to target different autoreactive cells and/or different subsets of autoreactive cells. This can also allow for the use of multiple and/or different signaling and recognition construct(s) to create logic gates that can direct KIT CAAR cell activity to specific combinations of receptors and/or cell types. This can be particularly valuable in the treatment of autoimmune disease, because there are often many different autoreactive cells that would need to be targeted. In various embodiments, a KIT CAAR system can be used to treat various medical conditions. In various embodiments, a medical condition can include a response, medical response, syndrome, and/or disease.

Figure 5:
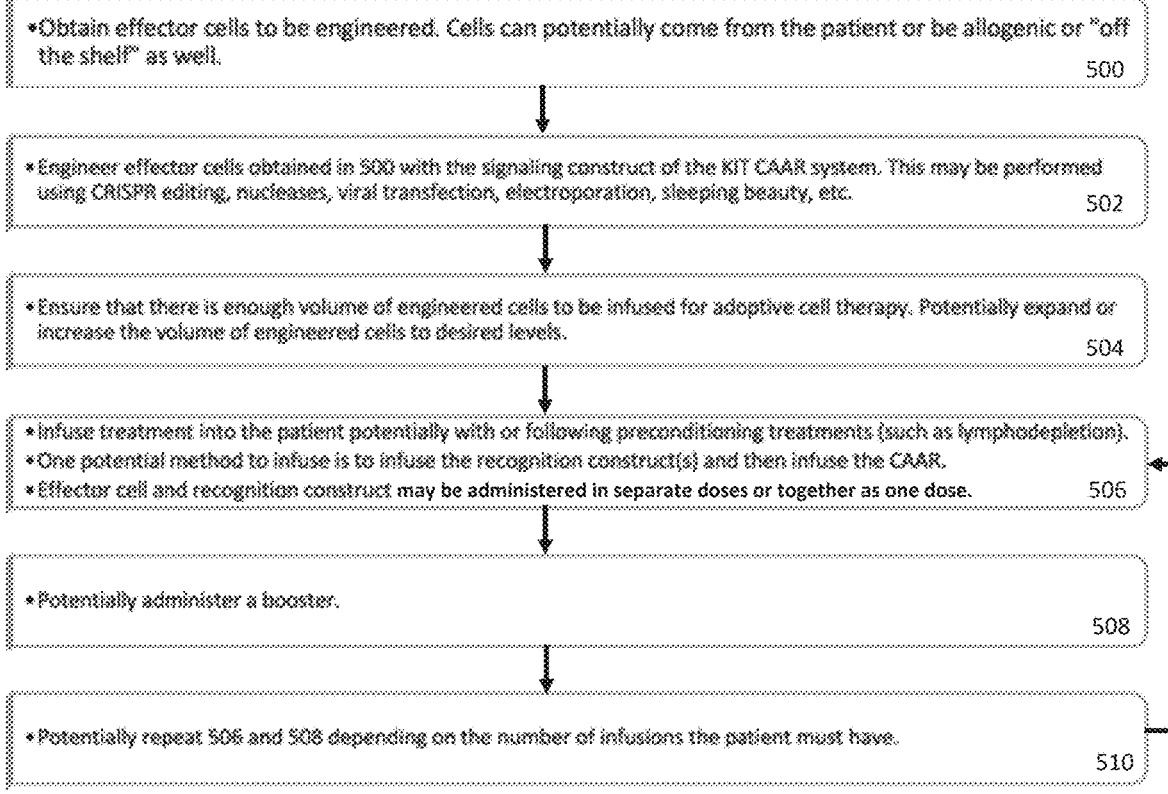
FIG. 5 is a flowchart of a potential application of the fragmented CAAR system demonstrating how the KIT CAAR may be used for therapeutic purposes, according to an illustrative embodiment.

The KIT CAAR can be employed in a number of ways, but typically as an adoptive cell therapy. FIG. 5 can be a flow chart of a potential application methodology of the KIT CAAR. At box 500, effector cells can be obtained, either the patient or from allogenic sources. At box 502, effector cells can be engineered to express the signaling construct of the KIT CAAR. This may be performed using a variety of gene editing methods, including but not limited to CRISPR, sleeping beauty, and viral transfection. At box 504, engineered effector cells can be assessed and potentially expanded to ensure that there can be enough engineered cells to infuse into the patient for the adoptive cell therapy. At box 506, the engineered cells can be infused into the patient potentially alongside or following preconditioning treatments (such as lymphodepletion). This might be via an intravenous method or through other means. One potential method is to infuse the recognition construct(s) and then infuse the CAAR. At box 508 a booster can potentially be administered into the patient, which may be an ancillary technology to enhance or modulate the KIT CAAR, or something that could affect the overall effectiveness of the treatment. This can also include infusion of a different embodiment of the KIT CAAR. At box 510, box 506 and/or box 508 can be repeated in subsequent administrations of engineered cells and/or booster. This can include an additional dose of components of the same KIT CAAR, or administration of components of a different KIT CAAR. By way of non-limiting example, box 510 can include administering multiple and unique recognition constructs.

Figure 6:
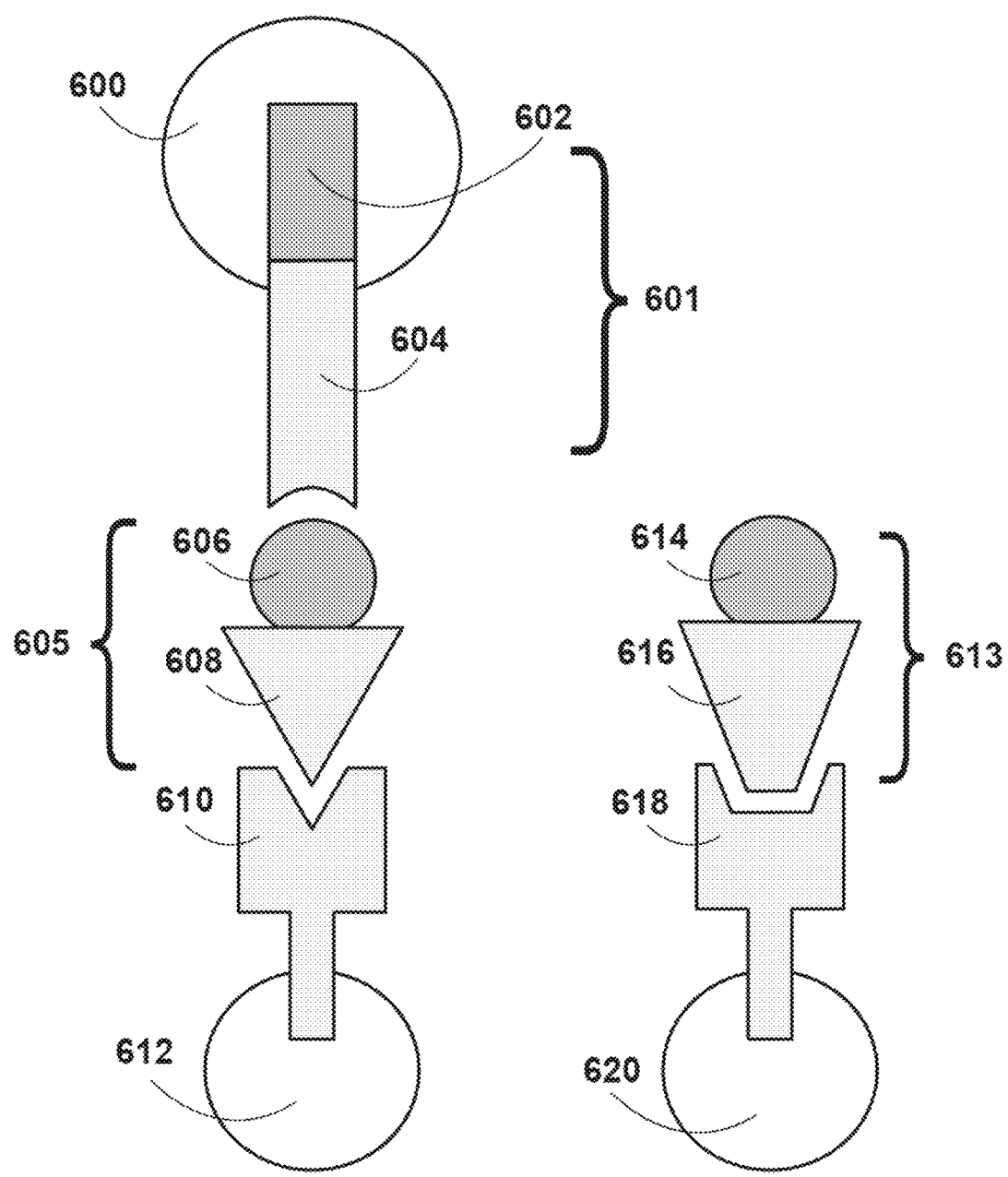
FIG. 6 is a schematic view of a fragmented CAAR system demonstrating how a second recognition construct can be used to target a second target ligand, according to an illustrative embodiment.

FIG. 6 describes an example of an additional composition of the KIT CAAR. Effector cell 600 can be engineered to express a transmembrane polypeptide signaling construct 601 that can include signaling domain 602 and signaling construct protein binding domain 604. Signaling construct protein binding domain 604 can bind to a first recognition construct 605 at recognition construct protein binding domain 606. The first recognition construct 605 can further include non-immunoglobulin moiety 608. Non-immunoglobulin moiety 608 can bind autoreactive receptor 610, which can be located on the target cell 612. The effector functions of effector cell 600 can be activated when the recognition construct 605 is bound to both autoreactive receptor 610 and signaling construct 601. The KIT CAAR can also contain a second recognition construct 613, which can include recognition construct protein binding domain 614 and non-immunoglobulin moiety 616. Recognition construct protein binding domain 614 can also bind signaling construct protein binding domain 604, and/or can compete for binding of signaling construct protein binding domain 604 with the recognition construct protein binding domain 606. In an embodiment, a recognition construct can be bound to an autoreactive receptor for competitive binding of a protein binding domain(s) to take place. In an embodiment, a recognition construct can't be bound to an autoreactive receptor for competitive binding of a protein binding domain(s) to take place. This type of competitive binding can allow effector cell 600 to be activated when different target receptors are bound by different recognition constructs. Non-immunoglobulin moiety 616 can bind autoreactive receptor 618, located on another target cell 620. The effector functions of effector cell 600 can also be activated when signaling construct protein binding domain 604 is bound to recognition construct protein binding domain 614 at the same time that non-immunoglobulin moiety 616 is bound to autoreactive receptor 618. The effector functions of effector cell 600 can be to release cytotoxic molecules to kill target cells. The effector functions of effector cell 600 can be to induce anergy. The effector functions of effector cell 600 can be to increase activation of the cell.

In various embodiments, the non-immunoglobulin moiety 608 can be an MHC-peptide complex or derived from an MHC-peptide complex. The KIT CAAR can be referred to as a CITE system if non-immunoglobulin moiety 608 is an MHC-peptide complex or derived from an MHC-peptide complex.

Figure 7:
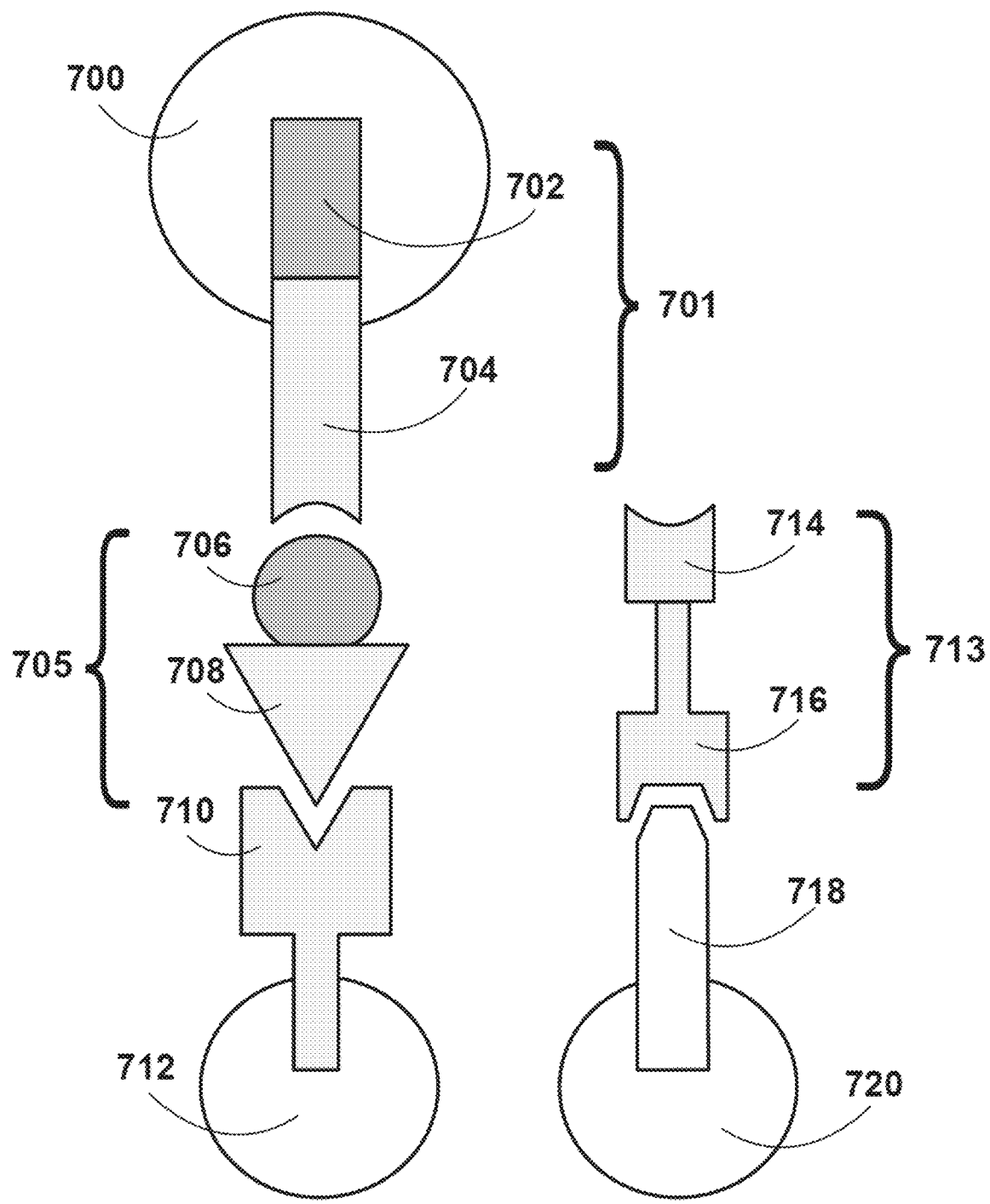
FIG. 7 is a schematic drawing of a fragmented CAAR system demonstrating how a second recognition construct can be used to prevent binding to healthy cells, according to an illustrative embodiment.

FIG. 7 describes an additional composition of the KIT CAAR. Effector cell 700 has been engineered to express a signaling construct 701 that includes signaling domain 702 and signaling construct protein binding domain 704. Signaling construct protein binding domain 704 can bind to a first recognition construct 705 located in extracellular space. The first recognition construct 705 includes recognition construct protein binding domain 706 and non-immunoglobulin moiety 708. Signaling construct protein binding domain 704 can bind recognition construct protein binding domain 706 and non-immunoglobulin antigen 708 can bind autoreactive receptor 710, located on target cell 712. Effector cell 700 can be activated when recognition construct 705 is bound to both signaling construct protein binding domain 704 and autoreactive receptor 710.

A second recognition construct 713 can include recognition construct protein binding domain 714 and moiety 716. Moiety 716 can bind to second ligand or receptor 718, expressed by a second effector cell 720, which can be a healthy cell. Recognition construct protein binding domain 714 can compete with signaling construct protein binding domain 704 for binding to recognition construct protein binding domain 706. This can reduce off target effects of engineered effector cell 700, since binding of recognition construct protein binding domain 714 to recognition construct 705 can prevent binding of recognition construct 705 to signaling construct protein binding domain 704. Preventing binding of recognition construct 705 to signaling construct protein binding domain 704 can prevent activation of signaling domain 702. Since second recognition construct 713 can be found in the presence of healthy cells, second recognition construct 713 can prevent activation of effector cell 700 in the presence of healthy cells, thereby reducing off-target effects.

Binding of recognition construct protein binding domain 706 to recognition construct protein binding domain 714 at the same time as binding of non-immunoglobulin moiety 708 to autoreactive receptor 710 and binding of moiety 716 to signaling domain 718 can activate effector cell 720.

In various embodiments, the non-immunoglobulin moiety 708 and/or moiety 716 can each be an MHC-peptide complex or derived from an MHC-peptide complex. The KIT CAAR can be referred to as a CITE system if non-immunoglobulin moiety 708 and/or moiety 716 are MHC-peptide complexes or derived from MHC-peptide complexes.

Figure 8A:
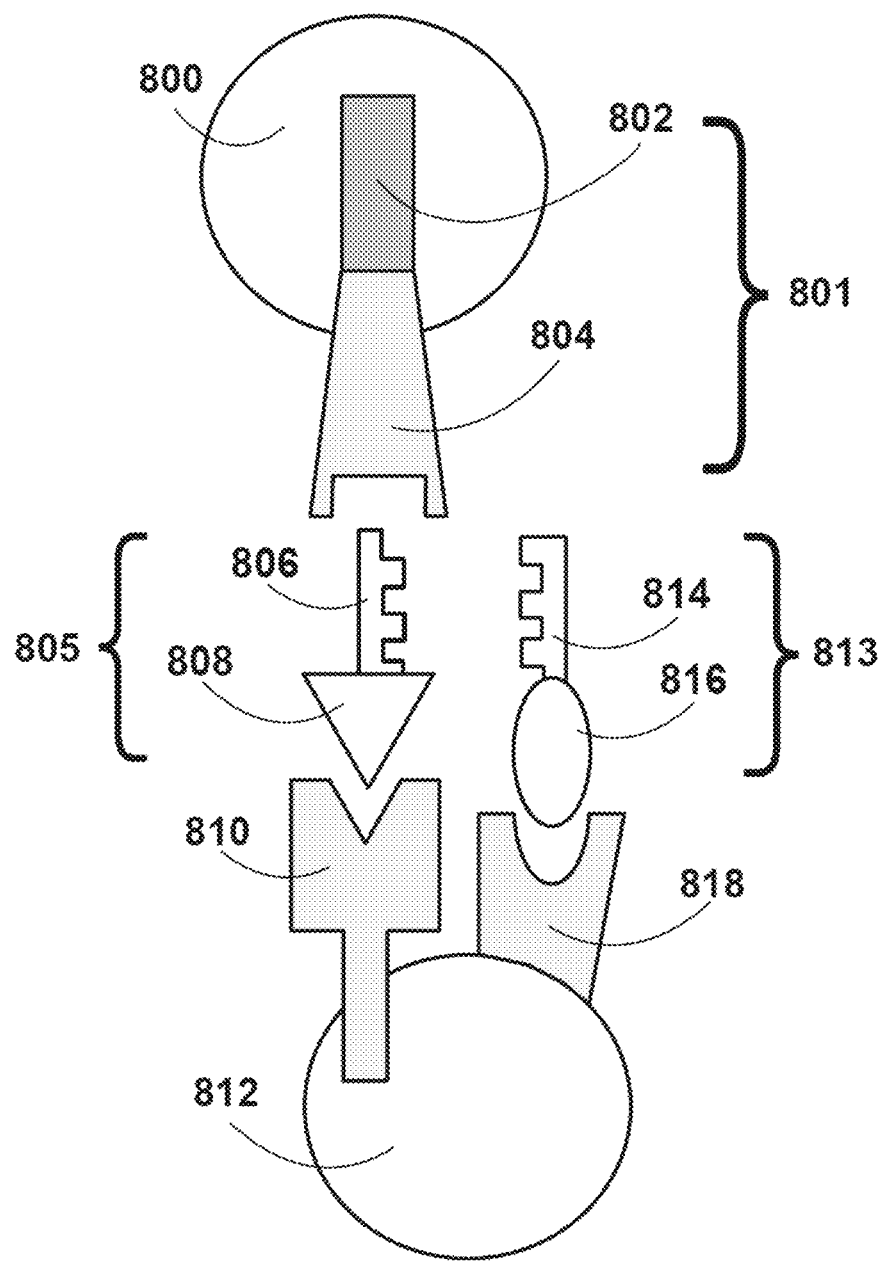
FIG. 8A is a schematic drawing of a fragmented CAAR system containing two recognition constructs demonstrating how a second recognition construct can be used as an "and" gate, according to an illustrative embodiment.

FIG. 8A describes an additional composition of the KIT CAAR. Effector cell 800 can be engineered to express a transmembrane polypeptide signaling construct 801 including signaling domain 802 and signaling construct binding domain 804.

Figure 8B:
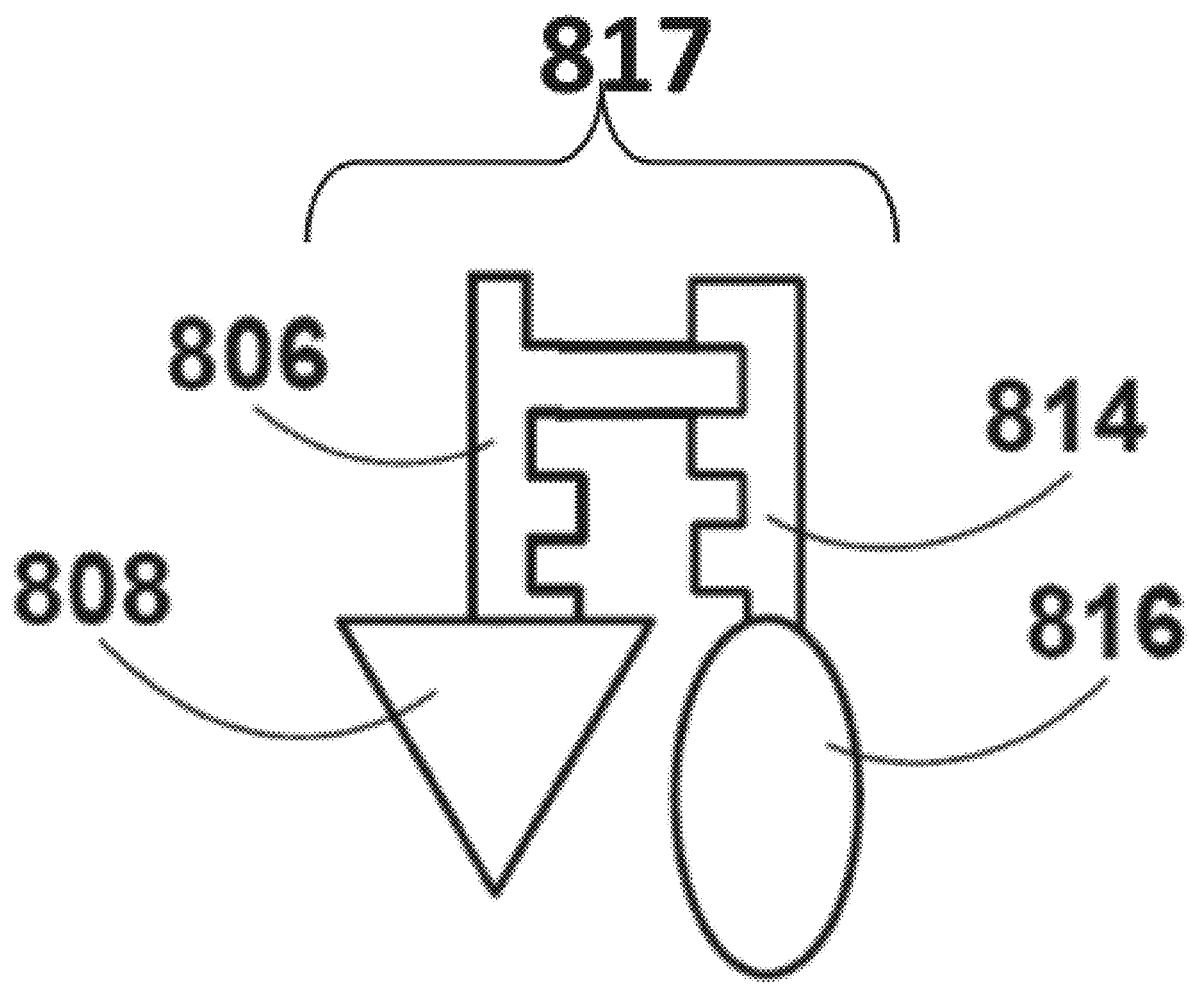
FIG. 8B is a schematic drawing of an embodiment of a combined recognition construct.

A first recognition construct 805 can include recognition construct binding domain 806 and non-immunoglobulin moiety 808. Non-immunoglobulin moiety 808 can bind autoreactive receptor 810, located on target cell 812. A second recognition construct 813 can include recognition construct binding domain 814 and moiety 816. Moiety 816 can bind moiety 818, also located on target cell 812. The recognition construct binding domain 806 of the first recognition construct 805 can bind to the recognition construct binding domain 814 of the second recognition construct 813 (as shown in FIG. 8B). This combination can bind to signaling construct binding domain 804. Signaling construct 801 can be activated when recognition construct binding domain 806 is bound to recognition construct binding domain 814, and the combination is bound to signaling construct binding domain 804 at the same time that non-immunoglobulin moiety 808 is bound to autoreactive receptor 810 and moiety 816 is bound to ligand 818. Activation of the signaling construct 801 can activate the effector functions of effector cell 800. A recognition construct binding domain can be referred to as a RCBD and/or recognitioncon binding domain.

In various embodiments, protein binding domain 806 and protein binding domain 814 can be complementary strands of ssDNA, and protein binding domain 804 can be a zinc finger domain.

In various embodiments, non-immunoglobulin moiety 808 and/or moiety 816 can each be an MHC-peptide complex or derived from an MHC-peptide complex. The KIT CAAR can be referred to as a CITE system if non-immunoglobulin moiety 808 and/or moiety 816 are MHC-peptide complexes or derived from MHC-peptide complexes. FIG. 8B describes an embodiment of a combined recognition construct 817. In an embodiment, a combined recognition construct can include a first recognition construct 805 and a second recognition construct 813. In an embodiment, a combined recognition construct can include a first recognition construct 805 bound to a second recognition construct 813. In an embodiment, recognition construct binding domain 806 can be bound to recognition construct binding domain 814.

Figure 9:
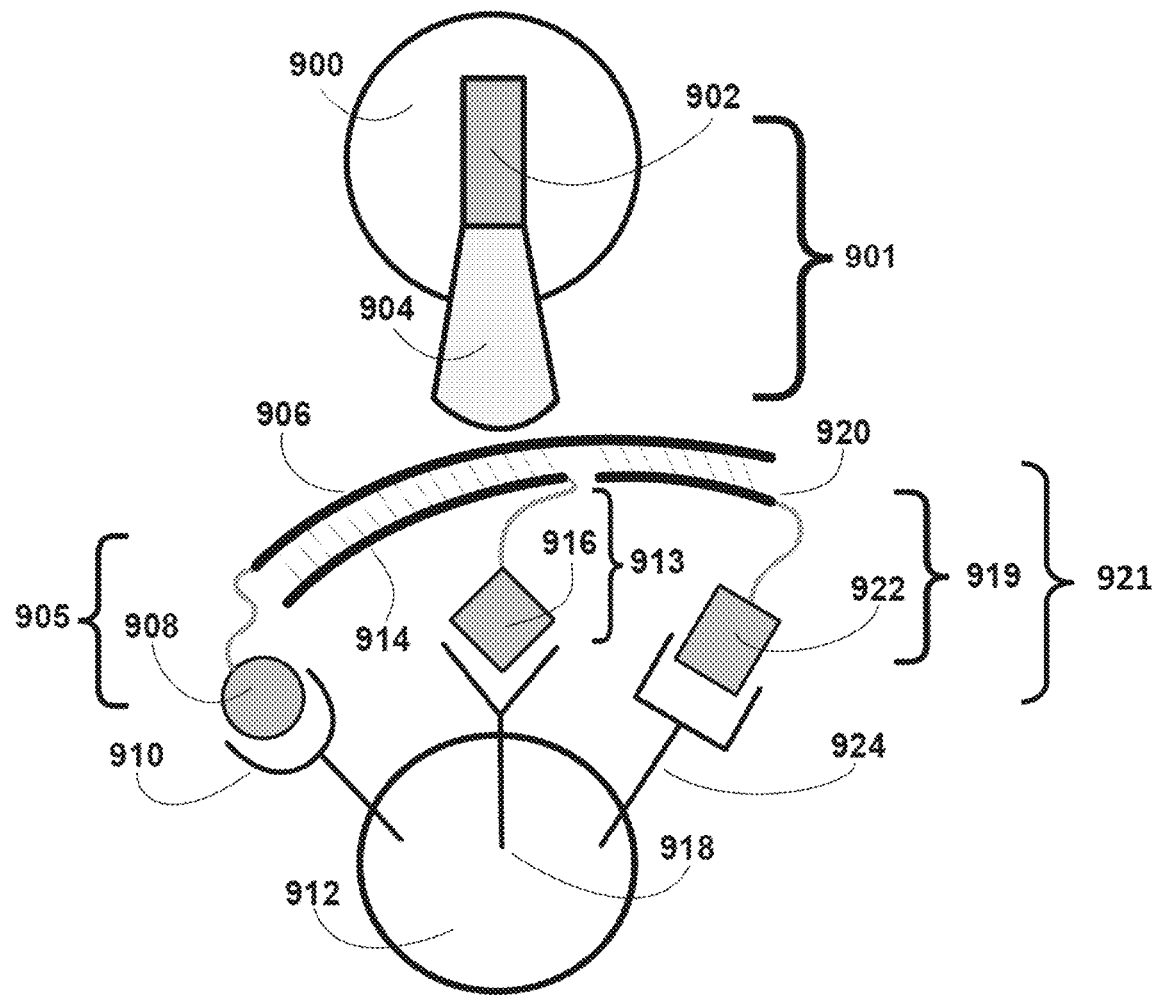
FIG. 9 is a schematic drawing of a fragmented CAAR system containing three recognition constructs, and demonstrating how three recognition constructs can be used as an "and" gate, according to an illustrative embodiment.

FIG. 9 depicts an example of another embodiment of a KIT CAAR. Effector cell 900 has been engineered to express transmembrane polypeptide signaling construct 901 that can include signaling domain 902 and protein binding domain 904. A first recognition construct 905 can include binding domain 906 and non-immunoglobulin moiety 908. Non-immunoglobulin moiety 908 can bind first autoreactive receptor 910 located on target cell 912. A second recognition construct 913 can include binding domain 914 and non-immunoglobulin moiety 916. Non-immunoglobulin moiety 916 can bind to second autoreactive receptor 918 also located on target cell 912. A third recognition construct 919 can include binding domain 920 and non-immunoglobulin moiety 922. Non-immunoglobulin moiety 922 can bind to second autoreactive receptor 924 also located on target cell 912.

In one embodiment, binding domain 914, binding domain 920, and binding domain 906 can be ssDNA. Binding domain 914 and binding domain 920 can both be complementary to non-overlapping parts of binding domain 906. Binding of all these components can form dsDNA, which can bind to protein binding domain 904. In an embodiment, binding of binding domain 906, binding domain 914, and binding domain 920 together can form binder complex 921, which can form dsDNA or be dsDNA. In an embodiment, joining of recognition constructs 905, 913, and 919 together can form binder complex 921, which can form dsDNA or be dsDNA In various embodiments, non-immunoglobulin moiety 908, non-immunoglobulin moiety 916, and/or non-immunoglobulin moiety 922 can each be an MHC-peptide complex or derived from an MHC-peptide complex. The KIT CAAR can be referred to as a CITE system if non-immunoglobulin moiety 908, non-immunoglobulin moiety 916, and/or non-immunoglobulin moiety 922 are MHC-peptide complexes or derived from MHC-peptide complexes.

Figure 10:
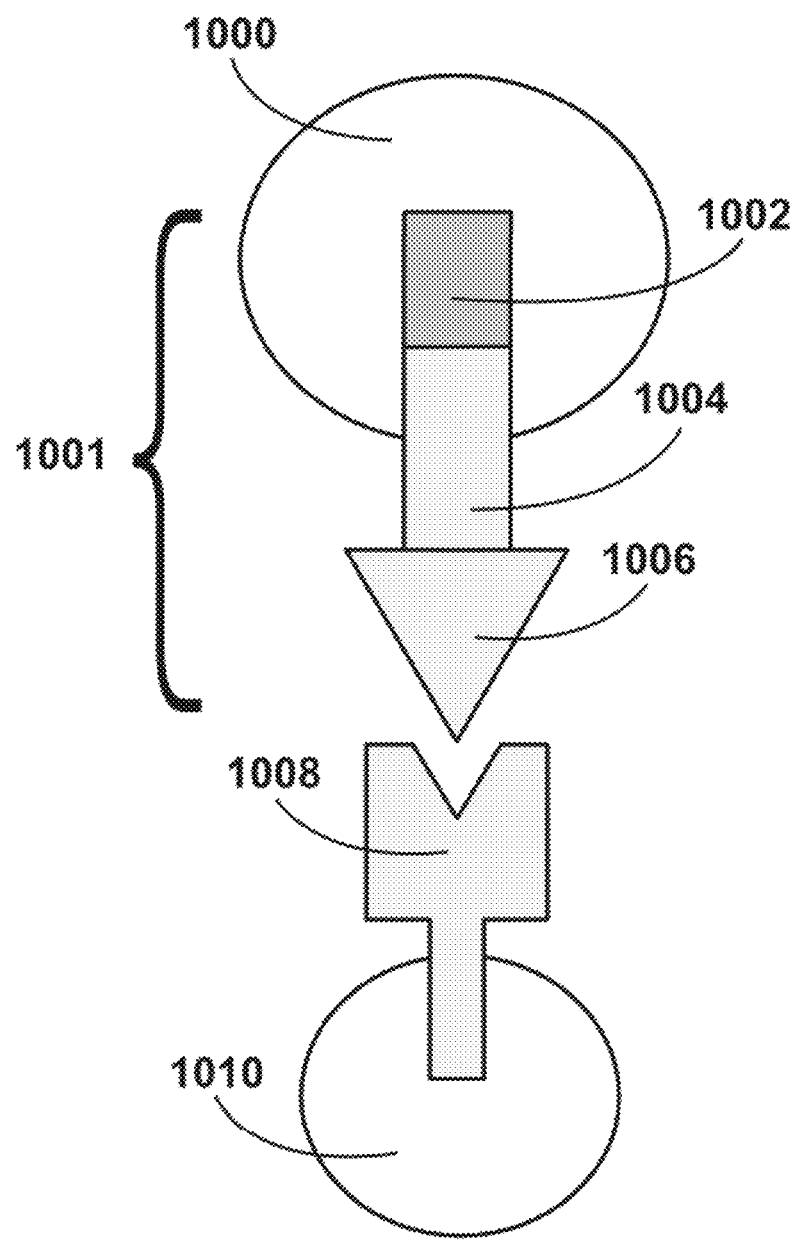
FIG. 10 is a schematic view of the components of a fused CITE system, as described herein according to an illustrative embodiment.

FIG. 10 is an example of a fused CITE system, which is a variation of the CITE system. A fused CITE system can include an effector cell 1000 which can be engineered to express CITE fusion protein 1001. CITE fusion protein 1001 can include signaling domain 1002, transmembrane domain 1004, and MHC-peptide complex 1006. The MHC-peptide complex 1006 is able to bind to a target T cell receptor 1008, which can be located on T cell 1010. Binding of MHC-peptide complex 1006 to target T cell receptor 1008 can activate signaling domain 1002. Activation of the signaling domain 1002 can activate the effector functions of effector cell 1000. Effector functions can lead to the death, anergy, or other change in behavior to target cell 1010. In various embodiments, the engineered effector cell can interact with a CITE system recognition domain, which can interact with a target TCR. This engineered effector cell be activated by recognition domain and induce killing of T cells expressing the target TCR. In various embodiments, the cell can have low affinity for antibodies bound to a Fc receptor, to minimize toxicity against non-autoreactive cells. The recognition domain of the fusion protein in the fused CITE system can be based on an MHC-peptide complex or MHC-peptide fusion protein. The fused CITE system recognition domain can be engineered to bind specifically to a target TCR, which can be a TCR directed against self-antigen. Binding of the fused CITE system recognition domain can activate the fused CITE system signaling domain. Also described are effector cells that have been engineered to express one or more fused CITE systems. In various embodiments, this engineered effector cell can interact with a target TCR and induce its effector functions selectively against T cells expressing the target TCR. The fused CITE system can be a fusion protein that can include a MHC-peptide recognition construct, a transmembrane domain, and a cell signaling domain. This fused CITE system can be expressed by engineered effector cells, and the MHC-peptide recognition construct can be extracellular. The recognition construct could bind to target T cell receptors, and activate the signaling domain of the engineered effector cells. CITE system engineered effector cell activation can lead to target cell death, anergy of the target cell, or other functions that affect the behavior of the target cell.

In various embodiments, the effector cell 1000 may be selected from any of the following: T cells, NK cell, NKT cell, macrophage, a cell line thereof, other effector cell(s), off-the-shelf (allogenic) approaches, and stem-cell derived approaches.

In various embodiments, the intracellular cell signaling domain 1002 contains domains derived from one or more proteins selected from the group consisting of: TCRC, TCR, FcRy, FcRp, CD3y, CD35, CD3s, CD3C, CD22, CD79a, CD79b, CD66d, CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), CD279 (PD1), DAP10, LAT, KD2C, SLP76, TRIM, ZAP70, and 41BB.

In various embodiments, the MHC-peptide complex 1006 can be constructed from any combination of the following: conventional amino acids, non-proteinogenic amino acids including amino acids that have undergone co-translational or post-translational modifications, amino acids that are intermediates in biosynthesis, synthetic amino acids not found in natural proteins, carbohydrates, nanoparticles, ribonucleoproteins, lipids, dsDNA, ssDNA, and RNA.

Figure 11:
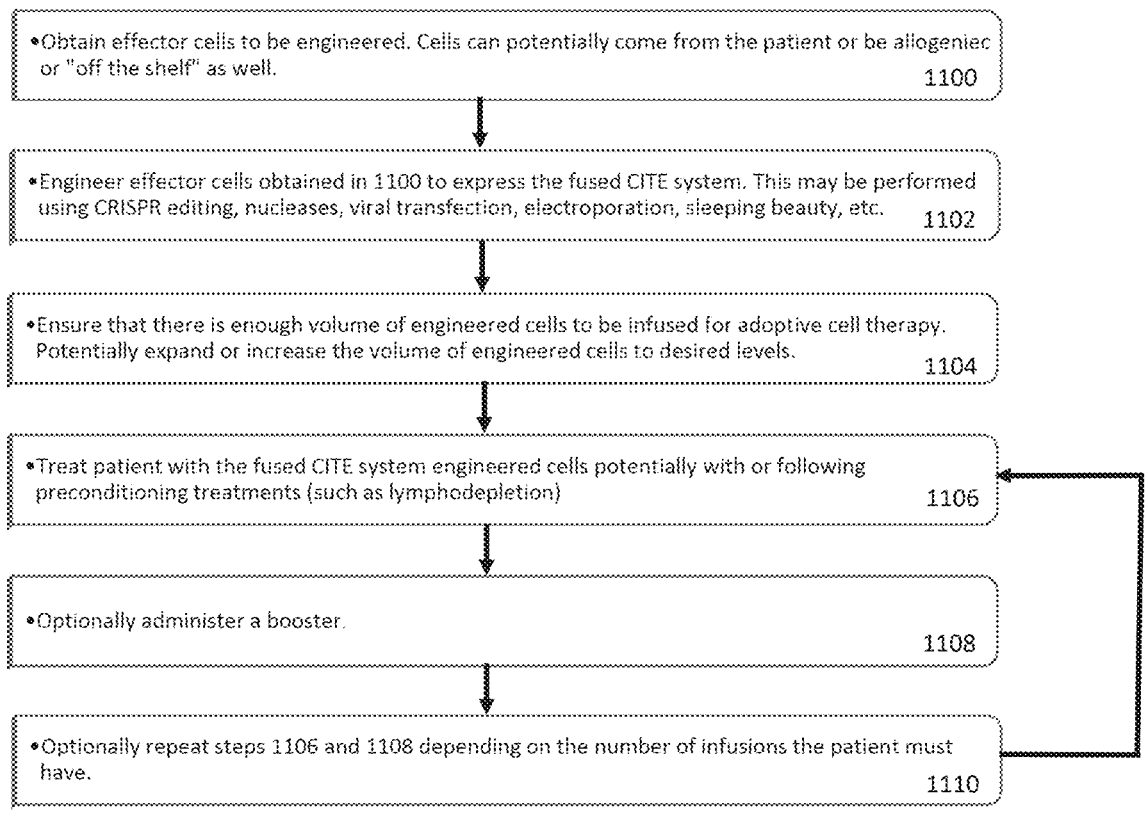
FIG. 11 is a flowchart of a potential application of a fused CITE system demonstrating how the fused CITE system may be used for therapeutic purposes, according to an illustrative embodiment.

The fused CITE can be employed in a number of ways, but typically as an adoptive cell therapy. FIG. 11 is a flow chart showing a potential application methodology of the fused CITE. At box 1100, effector cells are obtained, either the patient or from allogenic sources. At box 1102, effector cells are engineered to express the fused CITE system. This may be performed using a variety of gene editing methods, including but not limited to CRISPR, sleeping beauty, and viral transfection. At box 1104, engineered effector cells are assessed and potentially expanded to ensure that there are enough engineered cells to infuse into the patient for the adoptive cell therapy. At box 1106, the engineered cells are infused into the patient potentially alongside or following preconditioning treatments (such as lymphodepletion). This might be via an intravenous method or through other means. One potential method to treat patients is to inject engineered cells expressing the fused CITE system directly into the bloodstream.

At box 1108 a booster can potentially be administered into the patient, which may be an ancillary technology to enhance or modulate the activity of the cells engineered with fused CITE systems, or something that could affect the overall effectiveness of the treatment. This can also include infusion of cells engineered to express a different embodiment of the fused CITE system. At box 1110, box 1106 and box 1108 can be repeated in the subsequent administrations of engineered cells and/or booster. This can include an additional dose of cells engineered to express the same fused CITE, or administration of cells engineered to express different fused CITE(s).

The foregoing has been a detailed description of illustrative embodiments of the invention. Various modifications and additions can be made without departing from the spirit and scope if this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example a fragmented CAAR system may be used to treat a patient with bronchiectasis who produces autoantibodies towards bactericidal permeability increasing protein (BPI). Effector T cells extracted from the patient are transfected with a lentivirus construct that encodes the fragmented CAAR system signaling construct that can include transmembrane CD28-CD3 domain(s), and a BZip leucine zipper (RR) extracellular domain. A recognition construct with an autoantigenic BPI peptide fused to an AZip leucine zipper (EE) is synthesized separately. The BPI-based recognition construct is administered to the patient by joint injection into the patient's knee, followed by joint injection of the engineered effector T cells into the knee. Also for example, a CITE system may be used to treat a patient with type I diabetes who produces has autoreactive T cells towards preproinsulin. Effector T cells extracted from the patient are transfected with a lentivirus construct that encodes the CITE system signaling construct that includes transmembrane CD28-CD3 domains, and a BZip leucine zipper (RR) extracellular domain. A recognition construct with an autoantigenic preproinsulin peptide linked to MHC and AZip leucine zipper (EE) is synthesized separately. The preproinsulin-MHC based recognition construct is administered to the patient by blood transfusion, followed by blood transfusion of the engineered effector T cells. Additionally, as used herein, the terms "process" and/or "processor" should be taken broadly to include a variety of electronic hardware and/or software based functions and components (and can alternatively be termed functional "modules" or "elements"). Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. A system for selective depletion of autoreactive immune cells comprising:
   at least one cell engineered to express at least one signaling construct comprising an intracellular signaling domain and a signaling protein binding domain,
   at least one first recognition construct comprising
   a first non-immunoglobulin moiety specific for binding with an autoreactive receptor expressed by a first target autoreactive immune cell and
   a first recognition construct protein binding domain constructed to competitively bind to the signaling construct protein binding domain of the at least one engineered cell;
   and at least one second recognition construct comprising
   a second recognition construct protein binding domain constructed to competitively bind with to the signaling construct protein binding domain of the at least one engineered cell; and
   a second non-immunoglobulin moiety specific for binding with an autoreactive receptor expressed by a second target autoreactive immune cell.

2. The system of claim 1, wherein the first non-immunoglobulin moiety can bind to a target ligand found on a target cell associated with a medical condition selected from the group consisting of: autoimmune diseases, atopy, rheumatoid arthritis, cystic fibrosis, bronchiectasis, type I diabetes, celiac disease, inflammatory bowel disease, multiple sclerosis, autoimmunity, autoimmune response, vasculitis, myasthenia gravis, inflammatory diseases, inflammation, inflammatory response, neurological diseases, including Huntington's disease and Parkinson's disease, cardiovascular disease, including atherosclerosis, and infectious disease.

3. The system of claim 1, wherein at least one of the first and the second non-immunoglobulin moiety is selected from the group consisting of: affimers, DARPins, aptamers, affibodies, spiegelmers, autoantigen, MHC-autoantigen, MHC fragment, complexed MHC-autoantigen, complexed MHC fragment, MHC-peptide, complexed MHC-peptide, fused MHC-peptide, autoantigen fragment, autoantigen-based constructs, sugar-based constructs, and lipid-based constructs.

4. The system of claim 2, wherein the intracellular signaling domain is only activated when at least one of the at least one first recognition construct is bound to both the target ligand and the signaling protein binding domain of at least one of the at least one signaling constructs.

5. The system of claim 1, wherein the intracellular signaling domain is configured to activate or inhibit effector functions of the at least one engineered cell.

6. The system of claim 1, wherein the at least one engineered cell is selected from the group consisting of: T cells, NK cells, NKT cells, Treg, macrophages, a cell line, effector cells, allogenic cells, autologous cells, and stem-cell derivatives.

7. The system of claim 1, wherein at least one of the at least one first recognition constructs and at least one of the at least one signaling constructs are used to make at least one logic gate.

8. The system of claim 1, wherein the at least one engineered cell is further engineered to express at least one chimeric antigen receptor.

9. The system of claim 1, wherein an affinity for the binding by the first non-immunoglobulin moiety with the first target autoreactive immune cell is an order of magnitude greater than an affinity for binding by the first non-immunoglobulin moiety with the second target autoreactive immune cell.

10. The system of claim 1, wherein an affinity for the binding by the first non-immunoglobulin moiety with the first target autoreactive immune cell is two orders of magnitude greater than an affinity for binding by the first non-immunoglobulin moiety with the second target autoreactive immune cell.

11. The system of claim 1, wherein an affinity for the binding by the second non-immunoglobulin moiety with the second target autoreactive immune cell is an order of magnitude greater than an affinity for binding by the second non-immunoglobulin moiety with the first target autoreactive immune cell.

12. The system of claim 1, wherein an affinity for the binding by the second non-immunoglobulin moiety with the second target autoreactive immune cell is two orders of magnitude greater than an affinity for binding by the second non-immunoglobulin moiety with the first target autoreactive immune cell.

13. The system of claim 1, wherein the autoreactive receptor expressed by the first target autoreactive immune cell comprises a T cell receptor and the autoreactive receptor expressed by the second target autoreactive immune cell comprises a B cell receptor.

14. A system for selective depletion of autoreactive immune cells comprising:
at least one cell engineered to express at least one signaling construct comprising an intracellular cell signaling domain and a signaling construct protein binding domain;
at least one first recognition construct comprising
a first non-immunoglobulin moiety specific for a first autoreactive receptor expressed by a target autoreactive immune cell and
a first recognition construct protein binding domain that competitively binds to the signaling construct protein binding domain of the at least one engineered cell; and
at least one second recognition construct comprising
a second non-immunoglobulin moiety specific for a second autoreactive receptor expressed by the target autoreactive immune cell, and
a second recognition construct protein binding domain that competitively binds with the signaling construct protein binding domain of the at least one engineered cell.

15. The system of claim 14, wherein an affinity for binding by the first non-immunoglobulin moiety with the first autoreactive receptor is an order of magnitude greater than an affinity for binding by the first non-immunoglobulin moiety with the second autoreactive receptor.

16. The system of claim 14, wherein an affinity for binding by the first non-immunoglobulin moiety with the first autoreactive receptor is two orders of magnitude greater than an affinity for binding by the first non-immunoglobulin moiety with the second autoreactive receptor.

17. A system for selective depletion of autoreactive immune cells comprising:
at least one cell engineered to express at least one signaling construct comprising an intracellular cell signaling domain and a signaling construct protein binding domain;
at least one first recognition construct comprising
a first non-immunoglobulin moiety with a first affinity for binding with a first ligand of a target autoreactive immune cell and
a first recognition construct protein binding domain that competitively binds to the signaling construct protein binding domain of the at least one engineered cell; and
at least one second recognition construct comprising
a second non-immunoglobulin moiety with a second affinity for binding with a second ligand of a second target autoreactive immune cell, and
a second recognition construct protein binding domain that competitively binds with the signaling construct protein binding domain of the at least one engineered cell.

18. The system of claim 17, wherein each of the first affinity and the second affinity is an order of magnitude greater than an affinity for the first non-immunoglobulin moiety binding with a non-target cell.

19. The system of claim 17, wherein the first affinity is an order of magnitude greater than an affinity for the first non-immunoglobulin moiety binding with the second ligand.

20. The system of claim 17, wherein the ligand expressed by the first target autoreactive immune cell expresses a T cell receptor and the ligand expressed by the second target autoreactive immune cell expresses a B cell receptor.

* * * * *